US010641687B1

(12) United States Patent
St Amant, III

(10) Patent No.: US 10,641,687 B1
(45) Date of Patent: May 5, 2020

(54) WET GAS SAMPLE PROBE, VAPORIZING REGULATOR, AND METHODS ASSOCIATED THEREWITH

(71) Applicant: Mayeaux Holding LLC, Gonzales, LA (US)

(72) Inventor: Valmond Joseph St Amant, III, St Amant, LA (US)

(73) Assignee: MAYEAUX HOLDING, LLC, Gonzales, LA (US)

( * ) Notice: Subject to any disclaimer, the term of this patent is extended or adjusted under 35 U.S.C. 154(b) by 4 days.

(21) Appl. No.: 15/854,663

(22) Filed: Dec. 26, 2017

Related U.S. Application Data

(63) Continuation-in-part of application No. 15/615,772, filed on Jun. 6, 2017, now Pat. No. 10,436,678, and a continuation-in-part of application No. 15/653,083, filed on Jul. 18, 2017, which is a continuation-in-part of application No. 15/615,772, filed on Jun. 6, 2017, (Continued)

(51) Int. Cl.
| | |
|---|---|
| *G01N 1/22* | (2006.01) |
| *G01N 1/44* | (2006.01) |
| *G01N 33/22* | (2006.01) |

(52) U.S. Cl.
CPC ............. *G01N 1/2247* (2013.01); *G01N 1/44* (2013.01); *G01N 33/225* (2013.01)

(58) Field of Classification Search
CPC ............................ G01N 33/225; G01N 1/2247
USPC .......................... 73/863–864.91, 23.2–31.07, 73/335.01–335.14; 422/1–42, 50–98, 422/527–546, 109, 199, 244, 298, 299
See application file for complete search history.

(56) References Cited

U.S. PATENT DOCUMENTS

| | | |
|---|---|---|
| 2,515,835 A | 7/1950 | Preston |
| 3,080,760 A | 3/1963 | Piersma |

(Continued)

FOREIGN PATENT DOCUMENTS

| | | |
|---|---|---|
| CN | 201043965 | 4/2008 |

OTHER PUBLICATIONS

United States Patent Office, "Non-Final Rejection" in U.S. Appl. No. 14/214,225 (now U.S. Pat. No. 9,995,659), St Amant, III inventor, dated Jun. 5, 2017, 11 pages.

(Continued)

*Primary Examiner* — Robert R Raevis
(74) *Attorney, Agent, or Firm* — Joseph T Regard, Ltd plc

(57) ABSTRACT

A system for on-stream sampling of pressurized process gas such as natural gas or the like, said system optimized for use with pressurized process gas having liquid entrained therein, or otherwise referenced as "wet". In the preferred embodiment, a probe and method of sampling is contemplated to provide a linear sample of fluids from a predetermined area of said fluid stream. Further taught is the method of preventing compositional disassociation of a gas sample having entrained liquid utilizing a probe having a passage formed to facilitate capillary action in fluid(s) passing therethrough. The present system further contemplates a unique modular vaporizing pressure regulator formed to electrically engage a tube bundle via a tube bundle boot mounted on the bracket of a modular sample system in order to dispense with the need for conduit normally required for a separate power cord.

12 Claims, 29 Drawing Sheets

Related U.S. Application Data now Pat. No. 10,436,678, application No. 15/854,663, which is a continuation-in-part of application No. 15/228,814, filed on Aug. 4, 2016, now Pat. No. 10,073,013, application No. 15/854,663, which is a continuation-in-part of application No. 14/214,225, filed on Mar. 14, 2014, now Pat. No. 9,995,659.

(60) Provisional application No. 62/202,478, filed on Aug. 7, 2015, provisional application No. 61/798,287, filed on Mar. 15, 2013.

(56) References Cited

U.S. PATENT DOCUMENTS

| | | | |
|---|---|---|---|
| 3,133,444 A | 5/1964 | ERrnst | |
| 3,727,029 A * | 4/1973 | Chrow | F24H 1/142 |
| | | | 392/468 |
| 3,736,405 A * | 5/1973 | Bryson, Jr. | A47J 37/079 |
| | | | 219/270 |
| 4,086,922 A | 5/1978 | Henderson | |
| 4,100,806 A | 7/1978 | Barbonelle | |
| 4,283,947 A | 8/1981 | George | |
| 4,301,679 A | 11/1981 | Boyle | |
| 4,312,121 A | 1/1982 | Tweed | |
| 4,352,976 A * | 10/1982 | McMullan | A47C 21/048 |
| | | | 219/217 |
| 4,442,720 A | 4/1984 | Apley | |
| 4,537,071 A | 8/1985 | Waterman | |
| 4,625,570 A | 12/1986 | Witherspoon | |
| 4,688,537 A | 8/1987 | Calkins et al. | |
| 4,790,198 A | 12/1988 | Awtry | |
| 4,791,957 A | 12/1988 | Ross | |
| 4,993,842 A | 2/1991 | Morimoto | |
| 5,109,709 A | 5/1992 | Nimberger | |
| 5,154,087 A | 10/1992 | Wenshau | |
| 5,179,859 A | 1/1993 | Van Niekerk | |
| 5,237,878 A | 8/1993 | Hackenberg | |
| 5,440,941 A | 8/1995 | Kalidindi | |
| 5,501,080 A | 3/1996 | McManus et al. | |
| 5,531,130 A | 7/1996 | Welker | |
| 5,538,344 A | 7/1996 | Dybdahl | |
| 5,637,809 A | 6/1997 | Traina | |
| 5,746,586 A | 5/1998 | Fukuhara et al. | |
| 5,834,657 A | 11/1998 | Clawson et al. | |
| 5,894,080 A | 4/1999 | Dybdahl | |
| 6,325,843 B1 | 12/2001 | Hickox | |
| 6,357,304 B1 | 3/2002 | Mayeaux | |
| 6,605,475 B1 | 8/2003 | Taylor | |
| 6,701,794 B2 | 3/2004 | Mayeaux | |
| 6,869,800 B2 | 3/2005 | Torgerson | |
| 6,904,816 B2 | 6/2005 | Mayeaux | |
| 7,004,041 B2 | 2/2006 | Mayeaux | |
| 7,134,318 B2 | 11/2006 | Mayeaux | |
| 7,162,933 B2 * | 1/2007 | Thompson | G01N 1/2214 |
| | | | 73/863.11 |
| 7,471,882 B2 | 12/2008 | Peebles et al. | |
| 7,555,964 B2 | 7/2009 | Mayeaux | |
| 7,717,000 B2 | 5/2010 | Xie | |
| 7,942,065 B2 | 5/2011 | Xie | |
| 7,958,794 B2 | 6/2011 | Sahibzada et al. | |
| 8,196,480 B1 | 6/2012 | Mayeaux | |
| D674,052 S | 1/2013 | Thompson | |
| 8,522,630 B1 | 9/2013 | Mayeaux | |
| 9,200,986 B1 | 12/2015 | Mayeaux | |
| 9,257,027 B2 | 2/2016 | Williamson | |
| 9,395,280 B2 | 7/2016 | Thompson et al. | |
| 9,459,185 B2 | 10/2016 | Thompson et al. | |
| 9,535,427 B2 | 1/2017 | Patterson et al. | |
| 9,655,168 B2 * | 5/2017 | Belongia | H05B 3/0052 |
| 9,995,659 B1 | 6/2018 | St Amant, III | |
| 2005/0258142 A1 * | 11/2005 | Cho | H01L 21/67103 |
| | | | 219/50 |
| 2006/0229528 A1 | 10/2006 | Heske | |
| 2007/0158469 A1 | 7/2007 | Burgener | |
| 2007/0164562 A1 | 7/2007 | Valaskovic | |
| 2007/0217960 A1 | 9/2007 | Sekela | |
| 2010/0145634 A1 | 6/2010 | Pinguet | |
| 2010/0212757 A1 | 8/2010 | Patterson et al. | |
| 2010/0319468 A1 | 12/2010 | Peebles | |
| 2011/0036445 A1 | 2/2011 | Hall | |
| 2012/0033219 A1 | 2/2012 | Hokamura | |
| 2012/0325694 A1 | 12/2012 | Thompson | |
| 2013/0052083 A1 | 2/2013 | Kirby | |
| 2013/0220036 A1 | 8/2013 | Faust | |
| 2014/0041463 A1 | 2/2014 | Vethe | |

OTHER PUBLICATIONS

United States Patent Office, "Final Rejection" in U.S. Appl. No. 14/214,225 (now U.S. Pat. No. 9,995,659), St Amant, III inventor, dated Nov. 10, 2016, 13 pages.

United States patent Office, "Non-Final Rejection" in U.S. Appl. No. 15/615,772, St Amant, III inventor, dated Jan. 24, 2019, 13 Pages.

United States Patent Office, "Non-Final Rejection" in U.S. Appl. No. 15/653,083, St Amant III, Inventor, dated Apr. 8, 2019, 29 Pages.

ACME Cryogenics, ACME Model CV Cryogenic Valve Brochure, date unknown, US, p. 2.

ACME Cryogenics, Vacuum Insulated Pipe Brochure, date unknown, US.

Cryofab CFCL Series Vacuum Insulated Flexible Hose Product Sheet, date unknown, US.

Intertec, SL Blocktherm Self-Limiting Block Heater Product Sheet, HD-662ca, date unknown, US.

Intertec, Diabox 87 Product Sheet, KD222-12en DIABOX 87, date unknown.

A+ Corp, LLC, GENIE (tm) GPHV General Purpose Probe product sheet, SCC-GPHV-PS_0116 (0) 2012, US.

Thermon Manufacturing Co Brochure Form PAF0027-0714 "Installing Non-Heated Wires Within a Tube Bundle", Thermon Manufacturing Co, undated, US.

McMaster-Carr Supply Co, Web catalog at https://www.mcmaster.com/#catalog/123/1/=1ap8126, Stainless Steel Tubing, p. 153, undated, US.

ABB, Inc, TOTALFLOW NGC8206 Chromatograph User's Manual, (Copyright 2009, Ver 21015-002-rev.AE, US, See pp. 1-17, 2-25 & 2-58 through 2-64.

ACME Cryogenics, ACME Model CV Cryogenic Valve Brochure, date 2013, US, p. 2.

Federal Register, vol. 81, No. 222 BLM 43 CFR Parts 3175.111-112 "Onshore Oil and Gas Operations; Federal and Indian Oil and Gas . . . " Nov. 17, 2016, pp. 81578-81580 US.

ACME Cryogenics, Vacuum Insulated Pipe Brochure, date 2015, US.

ABB Inc, Portable NGC8206 Natural Gas Chromatograph DS_2101179, Copyright 2017, US.

Cryotab CFCL Series Vacuum Insulated Flexible Hose Product Sheet, date 2015, US.

A+ Corp LLC, Genie tm High Velocity Probe Product Sheet, PPS-SGP-HV-120803, Copyright 2003, US.

Intertec, SL Blocktherm Self-Limiting Block Heater Product Sheet, HD-662ca, date 2013, US.

Valtronics Inc, Mustang Sampling Sample Conditioning System MSCS P53, MSB-P53 vol. 1.2, (C) 2009, US.

Valtronics Inc, Mustang Sampling Pony Heated Probe Enclosure, MSB-PONYCS vol. 2.1, (C) 2009, US.

Welker Inc, Sample Conditioning Heated System Manual, Model SCHS, Manual IOM-132, Rev C, Apr. 20, 2016, p. 6.

Intertec, Diabox 87 Product Sheet, KD222-12en DIABOX 87, date 2017.

Mustang Sampling, LLC, MSCS Product Brochure, MSB-MSCS vol. 1.4, (C) 2009-2017, US.

Mustang Sampling, LLC, Solar Powered Sample Conditioning System SPSCS Product Brochure MSB-PonySOL vol. 2.1, (C) 2014-2017, US.

(56) References Cited

OTHER PUBLICATIONS

Mustang Sampling, LLC, Sample Conditioning System P53 Product Brochure MSBC-P53-CE vol. 2.2 (C) 2009-2017, US.
Mustang Sampling, LLC, PONY Heated Probe Enclosure Product Brochure MSBC-C-PONYCS vol. 4.4 (C) 2009-2017, US.
A+ Corp, LLC GENIE (tm) Heated Regulator GHR Product Sheet, SCC-GHR-PS_0906 (C) 2006, US.
A+ Corp, Genie (tm) GHR Heated Regulator Product Sheet, SCC-GHR0PS_1116, (C) 2012, US.
A+ Corp, LLC, GENIE (tm) GPHV General Purpose Probe product sheet, SCC-GPHV-PS_0116 (C) 2012, US.
A+ Corp, [LLC, GENIE (tm) Vaporizer Product Sheet, SCC-GV-PS_0106, C 2006, US.
A+ Corp LLC, Genie (tm) 760 Direct Drive Probe Product Sheet, SCC-7600PS 0116, A+ Corp LLC, Gonzales, LA, (C) 2012, US.
US Dept Interior, BOL Operator Letter (redacted), Jan. 19, 2017 regarding FMP's (Facility Measurement Points), Jan. 19, 2017, US.
Thermon Manufacturing Co Brochure Form PAF0027-0714 "Installing Non-Heated Wires Within a Tube Bundle", Thermon Manufacturing Co, 2014, US.
Mustang Sampling LLC, Mustang Intelligent Vaporizer Sampling System Model 2 Product Sheet, Mustang Sampling, LLC, Ravenswood WV, (C) 2009-2016, US.
Welker Inc, SCHS Sample Conditioning Heated System, Product Sheet, Welker, Inc, Sugar Land, TX, (C) 2016, US.
Matheson Gas, "The BTU Accuracy Connection to Profitability . . . ", Product Sheet, Matheson Gas, Montgomeryville, PA, 2010, US.
McMaster-Carr Supply Co, Web catalog at https://www.mcmaster.com/#catalog/123/1/=1ap8126, Stainless Steel Tubing, p. 153, 2016, US.
Research Gate discussion regarding capillary in Gas Chromatograph, Printed Dec. 15, 2017, https://www.researchgate.net/post/What_is_a_capillary_column_for_GC_and_how_does_it_work.
United States Patent Office, "Non-Final Rejection" in Utility U.S. Appl. No. 16/179,674, St Amant III, Inventor, dated Sep. 11, 2019, 9 Pages.
United States Patent Office, "Non-Final Rejection" in Utility U.S. Appl. No. 116/128,305, St Amant III, Inventor, dated Aug. 8, 2019, 8 Pages.
United States Patent Office, "Final Rejection" in Utility U.S. Appl. No. 15/653,083, St Amant III, Inventor, dated Jul. 16, 2019, 9 Pages.
United States Patent Office, Interview Summary in Utility U.S. Appl. No. 15/653,083, St Amant III, Inventor, dated Aug. 21, 2019, 2 Pages.
Mercado, Alexander, "Non-Final Rejection" U.S. Appl. No. 15/615,786, St Amant III, Inventor, dated Sep. 23, 2019, 12 pages.

\* cited by examiner

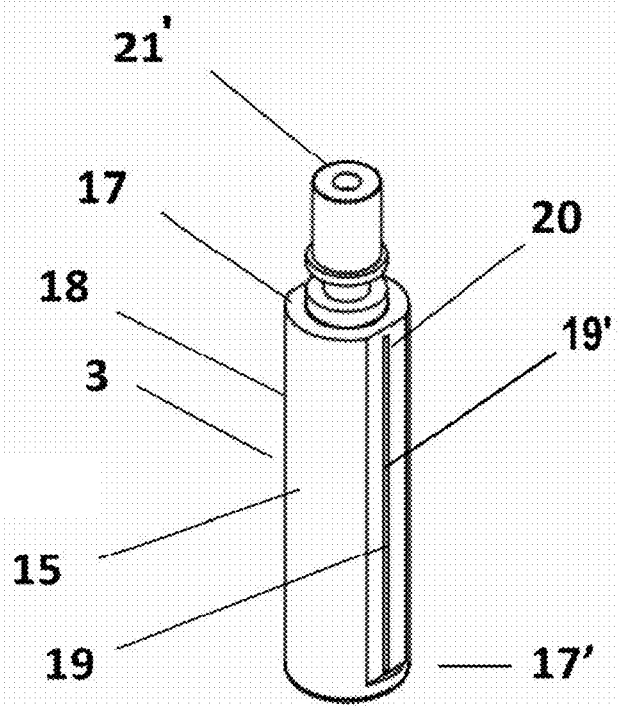

FIGURE 6A
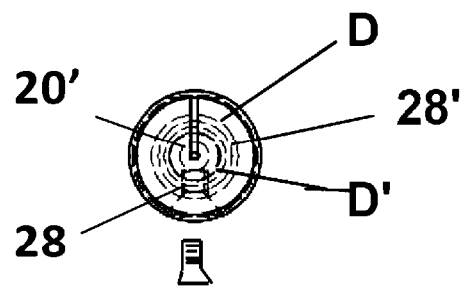
FIGURE 6B
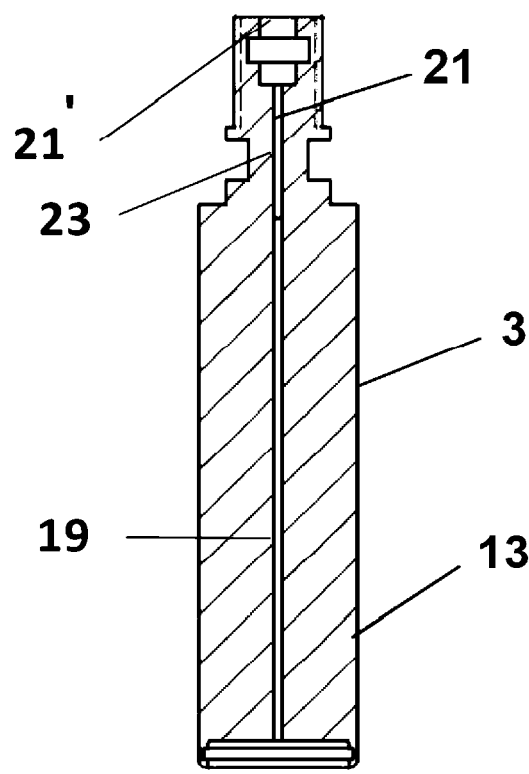
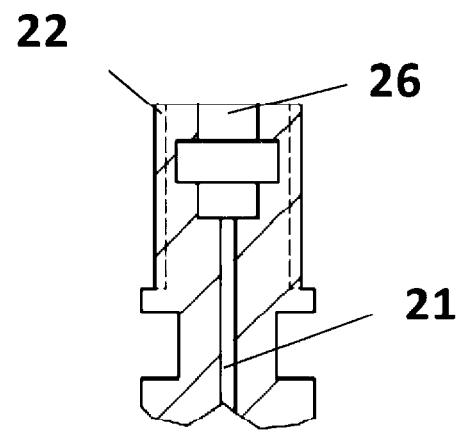
FIGURE 6C

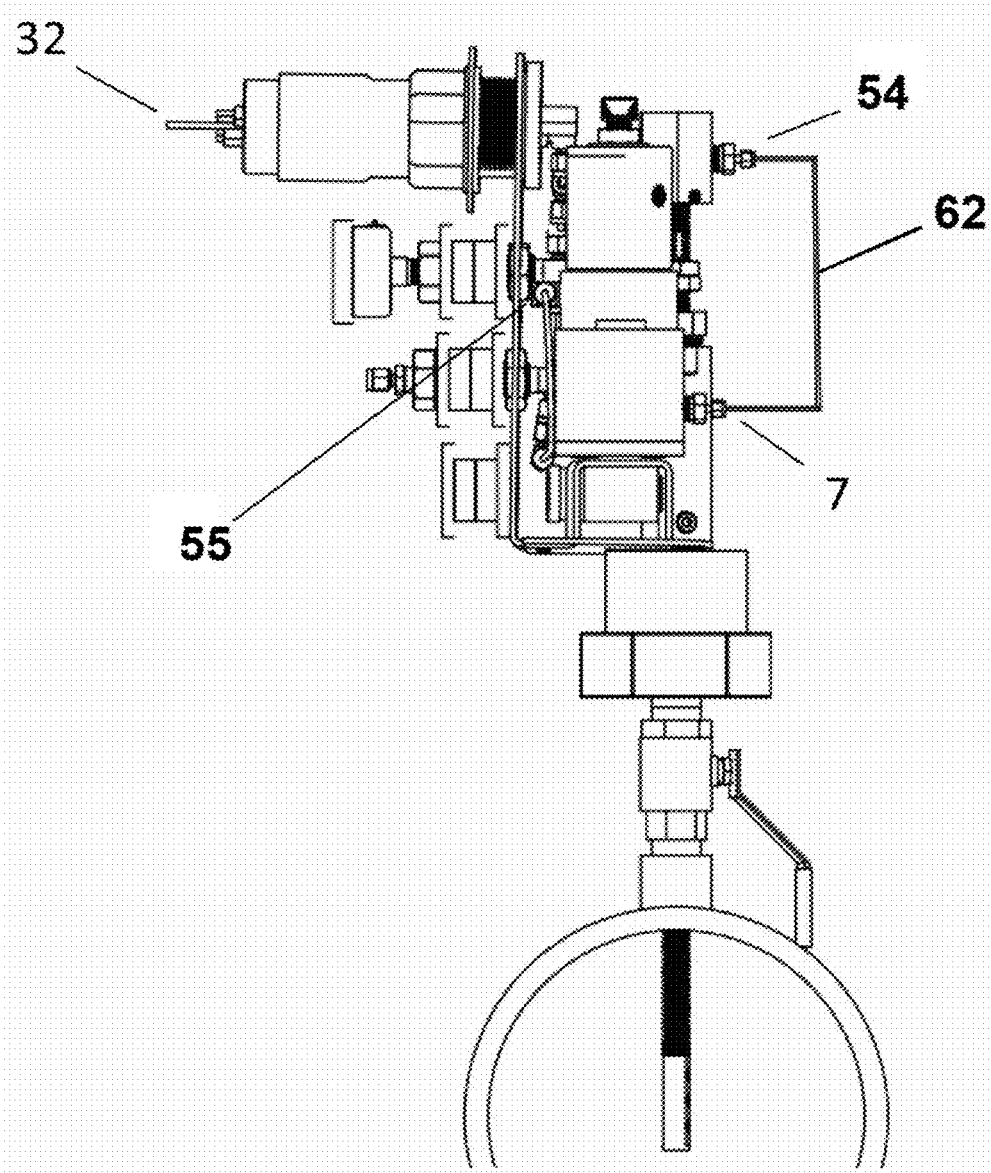

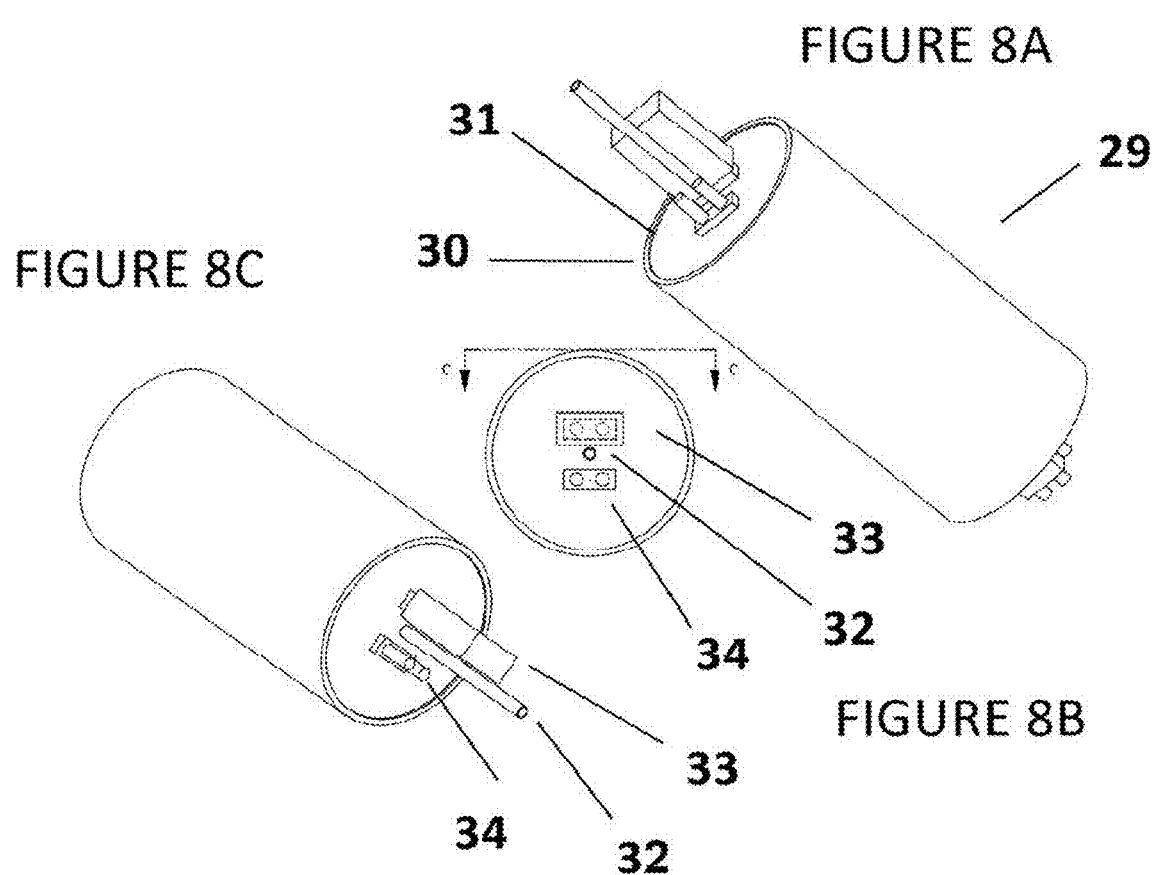

43

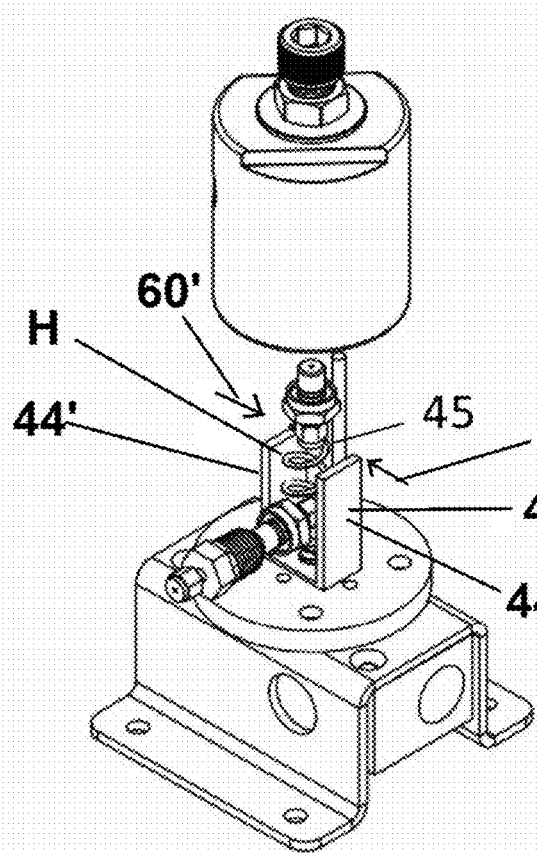
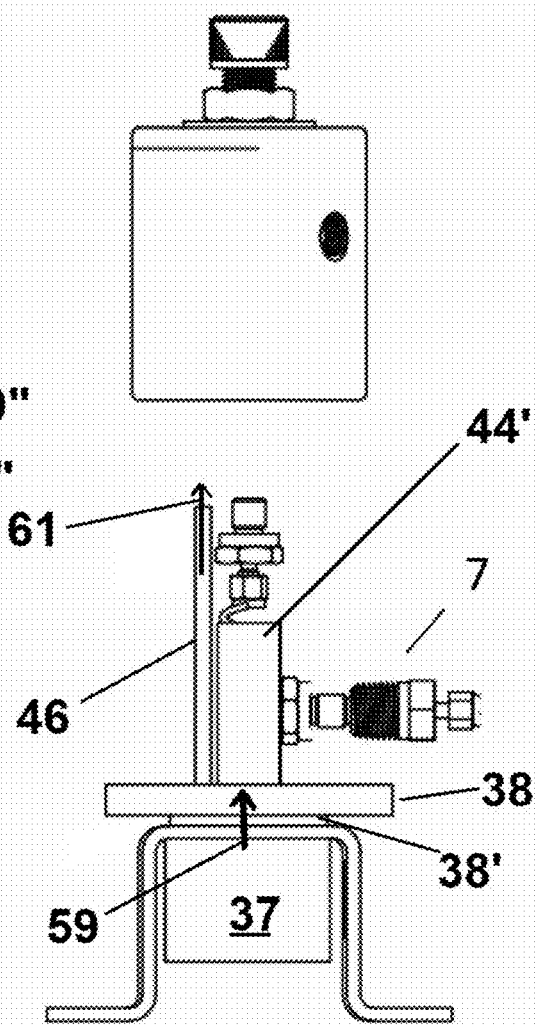
FIGURE 23A
FIGURE 23B

FIG 24A
FIG 24B
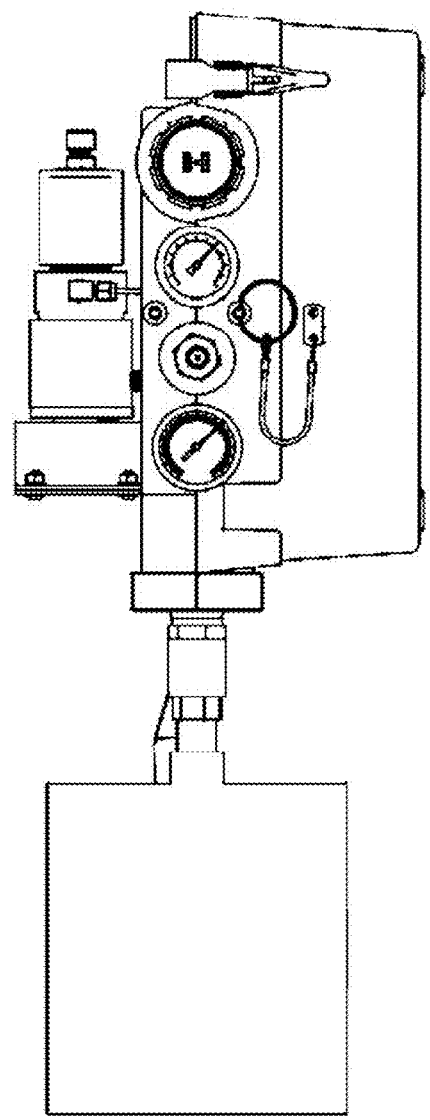
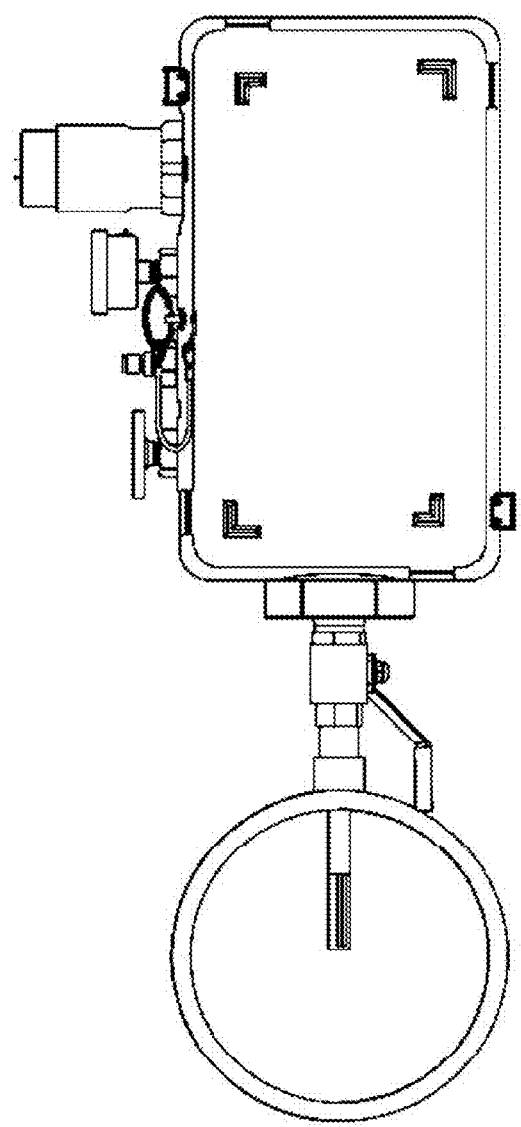

Prior Art

FIG 27A
FIG 27B
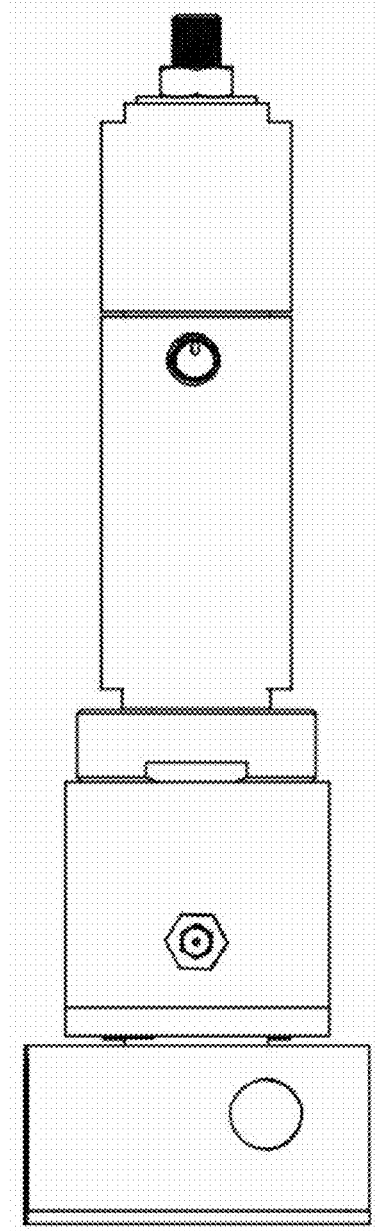
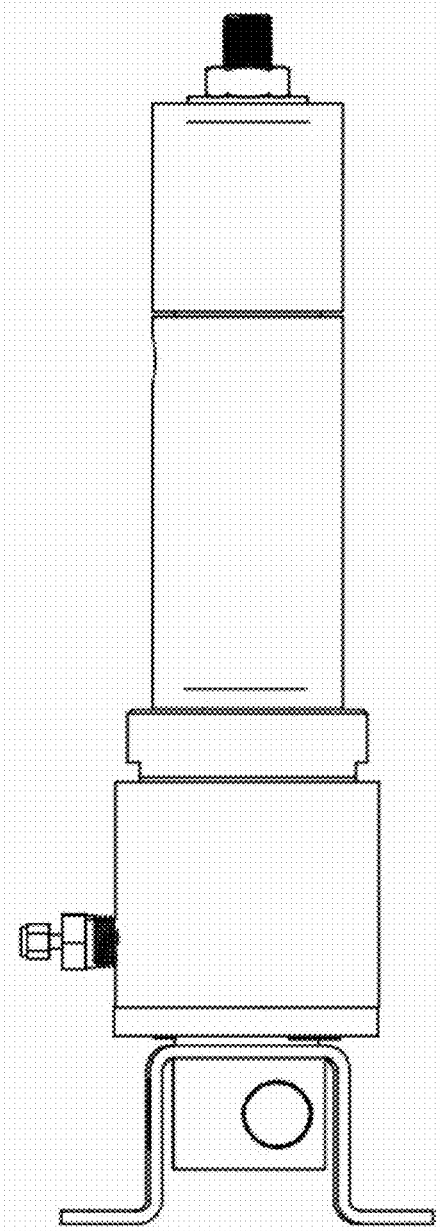

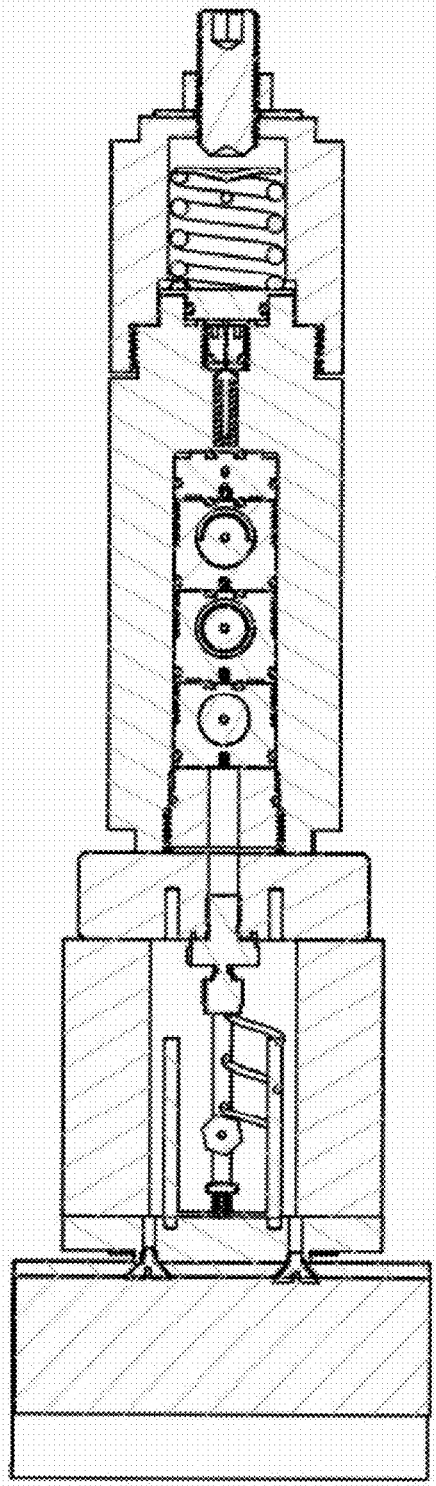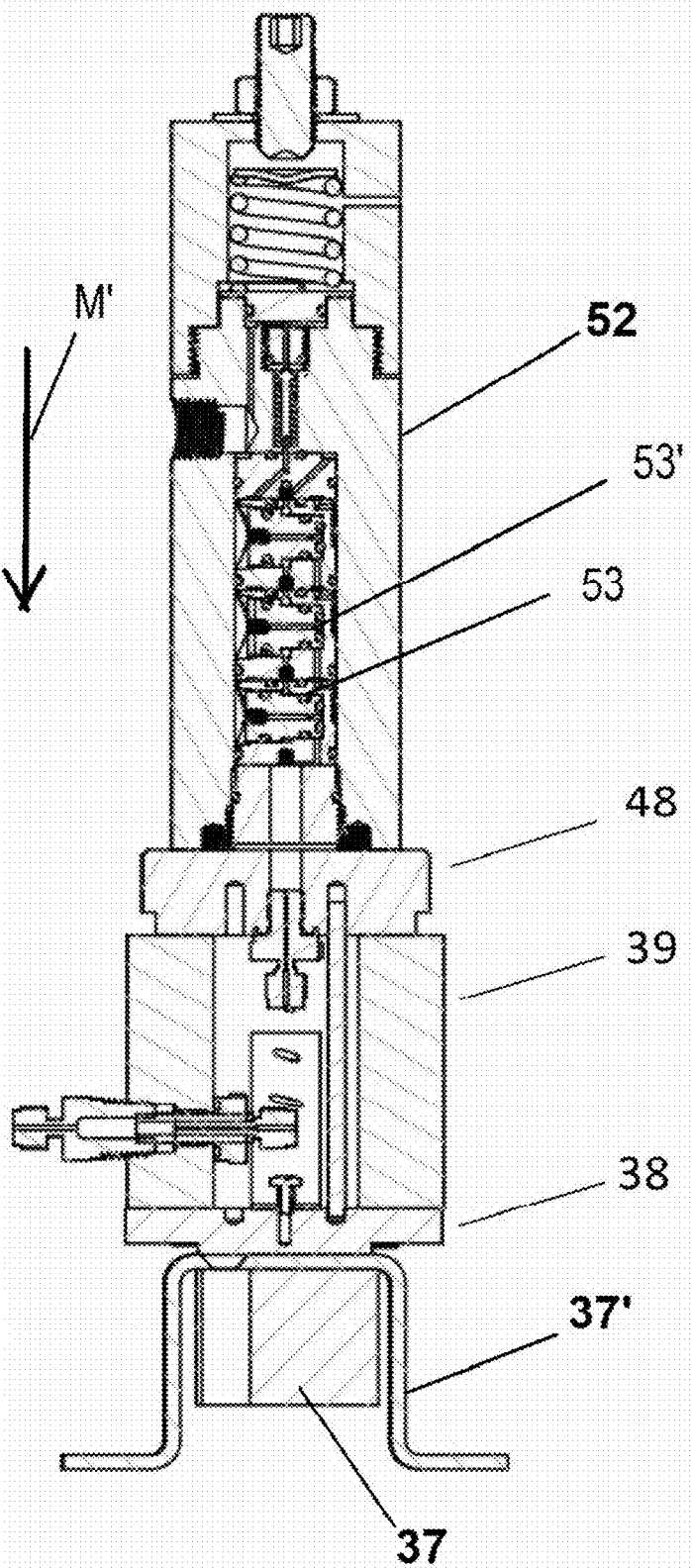

WET GAS SAMPLE PROBE, VAPORIZING REGULATOR, AND METHODS ASSOCIATED THEREWITH

STATEMENT OF CONTINUING APPLICATION

The present application is a continuation-in-part of U.S. Utility patent application Ser. No. 15/615,772 filed Jun. 6, 2017 entitled WET GAS SAMPLE SYSTEM, listing Valmond Joseph St Amant, III as inventor.

The present application is also a continuation-in-part of U.S. Utility patent application Ser. No. 15/653,083 filed Jul. 18, 2017 entitled WET GAS SAMPLE SYSTEM listing Valmond Joseph St Amant, III as inventor, said '083 case a continuation-in-part of U.S. Utility patent application Ser. No. 15/615,772 filed Jun. 6, 2017 entitled Wet Gas Sample System, listing Valmond Joseph St Amant, III as inventor.

The present application is also a continuation-in-part of U.S. Utility patent application Ser. No. 15/228,814 filed Aug. 4, 2016 entitled Source Mounted Modular Sample Conditioning System, listing Valmond Joseph St Amant, III as inventor, said '814 case claiming the benefit of Provisional Patent Application Ser. No. 62/202,478 filed Aug. 7, 2015, listing Valmond Joseph St Amant, III as inventor.

The present application is also a continuation-in-part of U.S. Utility patent application Ser. No. 14/214,225 filed Mar. 14, 2014 entitled WET GAS LATERAL SAMPLING SYSTEM AND METHOD, listing Valmond Joseph St Amant III as inventor, said '225 case claiming the benefit of Provisional Patent Application Ser. No. 61/798,287 filed Mar. 15, 2013.

FIELD OF THE INVENTION

The present invention relates to sampling of pressurized process fluids, and more particularly a system for on-stream and/or spot sampling of pressurized process gas having liquid entrained therein, otherwise known and referenced as multiphase or "wet" including but not limited to natural gas or the like. The present invention contemplates a unique and innovative probe formed to take a linear sample of fluids at a predetermined area of said fluid stream, including the center-third, in compliance with recent Bureau of Land Management (BLM) requirements, in combination with a tube bundle incorporating a separate power cord to power a modular vaporizing pressure regulator. The present invention provides a sampling system compliant with newly-revised BLM orders, and is particularly suitable for use in BLM regulated Facility Measurement Points (FMP). Also disclosed is a modular vaporizing regulator embodiment incorporating capillary flow and a bypass option particularly suitable for NGL applications.

BACKGROUND OF THE INVENTION

Natural Gas is comprised of a mixture of gases (See API 14.1 Section 6.3 and naturalgas.org). Natural gas is bought and sold based on its heating value (BTU), which is derived from a compositional analysis of the natural gas. It is the BTU content that determines the monetary value of a given volume of natural gas. This BTU value is generally expressed in decatherms (one million BTU).

To determine the total heat value of a given volume of gas, a sample of the gas is analyzed, and from the compositional data, its heat value per unit volume is calculated. This value is generally expressed in BTU/cu ft. The typical range of transmission quality gas ranges between 1000 and 1100 BTU/cu ft. Production gas, storage facility gas, NGL, and new found Shale Gas can have much higher heating values up to or even exceeding 1500 BTU/cu ft.

There has been a long-standing controversy between gas producers and gas transporters regarding entrained liquid typically present in most high BTU/cu ft. gas (rich or "wet" gas). Transporter tariffs require essentially liquid-free gas. Liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained liquid in any form.

Therefore, to fully comply with the current industry standards, membrane-tipped probes such as the A+ Corporation GENIE brand Probe (see U.S. Pat. Nos. 6,357,304, 6,701,794, 6,904,816, 7,004,041, and 7,134,318) have been used for many years to shed entrained liquids inside pressurized pipelines. Electrically powered heaters may be provided, which are powered by a separate power line included in the tube bundle. This power line is separate from the heat trace. These heaters are used to prevent hydrocarbon gas condensation in liquid-free gas samples.

Companies such as Mustang Sampling, LLC have bolted enclosures (See A+ U.S. Pat. No. 6,357,304, Hess U.S. Pat. No. 4,821,905, Thompson D674052, and Thompson U.S. Pat. No. 7,162,933, 2012/0325694) to the A+ Corporation membrane-tipped probes, and are believed to utilize third party, electrically-powered heater blocks (Intertec Hess) and A+ Corporation cartridge-type heated regulators for the enclosure, as well as third party electrical heat trace products. See for example U.S. Pat. No. 7,162,933. See also U.S. Pat. No. 9,459,185 relating to a solar powered sample analyzing system. See also ABB NGC8206 User Manual, Copyright 2009, Pages 1-17 and 2-58 through 2-64, available for download at their website.

Other housing or enclosure providers include, for example, vendors such as Intertec Hess GmbH's instrumentation component offerings on the internet at www.Intertec.info—Intertec Hess is not only a provider of enclosures but is also a provider of the electrically-powered heater blocks. Splicing kits suitable for such an application may be found at Protherm Industries Inc website, which offers, for example, a FE Series Splice Kit which could be used in this application; splice kits also available from other third-party providers such as Pentair at their website.

Mustang Sampling, LLC Brochures MSB-PONY and MSB P53, available at their website, can include products incorporating A+ Corporation GENIE brand membrane tipped probes, and utilize third party, electrically-powered heater blocks and A+ Corporation cartridge-type heated regulators and third-party heat trace, as described above. Mustang Sampling brochure MSB P53 illustrates a product which can include A+ Corporation GENIE brand membrane separators (U.S. Pat. No. 7,555,964, a CIP of 7097693 (listing the present Inventor as second Inventor)) in an enclosure, which is ideally mounted in the vicinity of the analyzer, which may include additional electrically-powered heater blocks and electrically powered heated regulators (See Mayeaux U.S. Pat. No. 6,357,304, Mayeaux U.S. Pat.

No. 8,220,479, Thompson U.S. Pat. No. 7,162,933, and Thompson US 2012/0325694 A1).

Other prior art includes the applicant assignee's (Mayeaux Holding, LLC/A+ Manufacturing, LLC) GENIE brand Vaporizer (FIG. 25) and GENIE brand Heated Regulator (FIG. 15) both commercialized in 2004, and GENIE brand JTR multi-stage regulator Mayeaux U.S. Pat. No. 8,220,479 and the GENIE brand membrane separator with liquid block (U.S. Pat. No. 7,555,964, a CIP of U.S. Pat. No. 7,097,693 (listing the present Inventor St. Amant as second Inventor with a priority date of 1996)) in an enclosure. Also see Thompson U.S. Pat. No. 9,285,299B2.

Other companies such as Welker Engineering use non-membrane probes (fixed probes) and bring the liquids outside the pipeline to reject the liquids inside enclosures containing an electrically powered heated regulator and then returning the liquid back to the pipeline, while hanging a hinged enclosure onto the probe (see Welker SCHS manual, page 6, at their website, and U.S. Pat. No. 7,471,882). The purpose of these sample systems is to reject entrained liquids and maintain the sample system temperature above the sample dew point to prevent further condensation.

The above and other known prior art rely upon power being readily available for electrical cartridge heater devices and electrical heater blocks to provide heat for the sample systems to prevent condensation in liquid-free gas samples, not to vaporize liquids. Vacuum jacketed tubing has also been used commercially for liquified natural gas sample systems for decades to insulate and preserve sample temperature. Vacuum jacketed tubing providers include companies like Acme Cryogenics and Cryofab. Also see Thompson U.S. Pat. No. 9,395,280 B2.

Recently the Bureau of Land Management (BLM) has revised 43 CFR 3175 (Order 5) The Onshore Oil and Gas Operations, Federal and Indian Oil and Gas Leases, Measurement of Gas effective Jan. 17, 2017, as indicated in the Federal Register, Vol 81, No 222, Sections 3175.111 and 3175.112, pages 81578-81580, issued 17 Nov. 2016.

Sections 3175.111 and 3175.112 now mandate a sampling protocol that is outside of the scope of API 14.1 and GPA 2166, by mandating sampling of two-phase samples (gas with entrained liquids) without rejecting the liquids, to provide a sample to the analyzer.

The above BLM order tries to reference parts of API 14.1 and GPA 2166, but it is clearly outside the scope of both of those industry standards. Further, said BLM order forbids the use of membranes or any other type of filter and means of liquid rejection in the probes used to take the sample. Therefore, under this BLM order as it presently stands, it appears that contaminants like glycols and amines cannot be rejected, filtered, or removed from the sample that is taken from the pipeline. In addition, the present BLM order requires liquids and gases to be removed from the center third of the pipeline, as well as heated sample lines to vaporize any liquids removed before they reach the analyzer.

Some of these sample points under the above referenced BLM order are in Facility Measurement Points (FMP) areas having electrical power availability. The power available may be 110V AC at high volume FMP sites or 24V DC at low volume FMP sites. The 24V DC available may be from solar power. Solar power has been traditionally used in natural gas sampling for decades, for example see U.S. Pat. No. 5,501,080A to McManus et al, claiming a 1994 Priority date, as one example as well as Thompson U.S. Pat. No. 9,459,185, and vendors such as ABB (See the ABB NGC8206 user manual pages 1-17 and 2-58 through 2-64, copyright 2009, available at the company website).

Under the above referenced BLM order, these BLM sample points will be required to not just heat the sample to prevent condensation of liquid-free gas, but to vaporize the entrained liquids removed with the gas samples. The BLM regulated locations with low volume FMPs may utilize portable low power gas analyzers that are powered from the technician's vehicle instead of on-site stationary conventionally powered gas analyzers such as gas chromatographs or other types of gas analyzers.

GENERAL SUMMARY DISCUSSION OF THE INVENTION

The present invention is configured to provide a single-phase gas sample to the analyzer without rejecting the liquids, the present system designed to be compliant with and particularly suitable for use in BLM regulated FMP areas, providing a unique sample system which is compliant with new BLM order 5, and without the problems and shortcomings associated with the prior art sample systems referenced above.

The present invention does not require the use of membrane filters or any other filter or method that would reject liquids. The present system contemplates a unique probe formed to take a linear sample of fluids at the medial area of said fluid stream, including the center-third, when required. The unique design and method of operation makes it particularly suitable for BLM order 5, providing compliant sample probes and methodologies. The present invention is also uniquely designed to not just provide heat to prevent condensation in liquid-free gas samples, but to vaporize the multiphase sample utilizing a separate power cord in the tubing bundle.

Unlike the above discussed, prior art sampling systems, the present invention teaches a new and innovative "integral slice" sampling process, wherein a very thin slice of the total volume of the source fluid flowing through a conduit or pipeline is captured by a streamlined container arrangement suspended in said source fluid, in a similar manner to an integral in calculus—a limiting procedure which approximates the area of a curvilinear region by breaking the region into thin vertical slices—with nominal flow disturbance, and in which trapped fluid is subsequently withdrawn and isolated in a location outside of the source fluid flowing stream.

Further, unlike dynamic isokinetic techniques, the system of the present invention insures that the representative sample taken either in spot, batch or continuous fashion is not allowed to disassociate due to the very small internal cavity of the slot and outflow passage following the slot. Empirical testing verifies that, if the diameter of the passage is sufficiently small, then the combination of surface tension (which is caused by cohesion within the liquid and adhesive forces between the liquid and container wall) and the higher velocity sweep will act to propel the liquid as well as the gas, preventing disassociation. The pipeline area is very large compared to the probe's very small interior and because of this vast difference; fluid in the probe will always be of a higher velocity than the pipeline fluid.

The high gas velocity (higher than the source velocity of the pipeline) of the very small internal cavity would then sweep all of the liquid particles at the same velocity as the gas particles being transported from the source to the probe. Therefore, it would remain "associated" with the gas from which it condensed. Small particles such as that which comprise smoke are known to behave somewhat like large molecules. High velocity gas in the small internal diameter bore of the probe will prevent any significant layer of liquid from accumulating on the surfaces. Even if an ultra-thin layer were to coat the probe's interior, the total area is so small that the impact would be negligible.

The present invention provides a far superior sampling solution for wet gas streams, including high HC dew point gases, which traditionally have been difficult to sample dynamically due to phase changes and resulting composition changes which can be triggered by flow, pressure, and/or temperature.

The present invention is a unique sample system designed to solve the problems of prior art sample systems while complying with the new BLM order 5.

The inlet of the present invention features a capillary passage following the linear-slot probe. The capillary passage may be in the form of a passage formed in the probe or capillary tubing inserted therein. In either case, the passage is formed to facilitate capillary action or motion, and higher velocity in "wet gas" flowing therethrough, to prevent the two-phase sample from disassociating as it is transported to the modular vaporizing pressure reducing regulator.

As discussed above, prior art systems that were designed to reject or remove liquids from the gas sample utilized electricity to power electrical devices such as heater blocks. Similarly, prior art systems utilized electricity to power heated regulators to prevent condensation in liquid-free samples due to JT cooling associated with pressure reduction of a gas or cold ambient environments that could cool the sample below its hydrocarbon (HC) dew point.

However, the additional electrical power required to not just overcome JT cooling due to the pressure reduction in liquid-free gas samples, or to offset ambient temperatures, but to in addition now vaporize liquids as required in BLM regulated FMP sites adds additional electrical load so as to overcome the latent heat of vaporization. Such an additional load may surpass the limited available power coming from the heat trace, which traditionally was tapped for relatively low power electrical needs.

Rather than relying on power from the heat trace, the present invention provides a separate power cord in a customized tube bundle for utilization as the power source. The power cord may bring, for example, 110V AC or 24V DC to the modular sample system utilizing the tube bundle. The power cord may be connected to a modular vaporizing regulator, vaporizers or regulators or other powered modular components of the two-phase sample system. Being "modular" each component provides one or more functions, as further described herein, and typically are relatively self-contained to provide the desired functionality, which can include, for example, conditioning (i.e, vaporizer, regulator, etc), monitoring (i.e., temperature or pressure), flow control (valve, etc) or other functions. This allows one to select and arrange one or more such components in a pre-determined flow pattern to facilitate the desired conditioning (or monitoring or other functions as described herein) of fluid(s) passing therethrough, and can as such provide a customized configuration in a modular sample system. The regulator may be, for example, a single stage or multistage regulator such as the assignee's U.S. Pat. No. 8,220,479 GENIE brand JTR (FIG. 26), the contents of which are incorporated herein by reference. An economic advantage to the power cord in the tube bundle is gained by eliminating the need for the long runs of conduit and multiple conduit fittings.

With the above discussed innovations, the present invention provides a novel and unique modular conditioner/sampling system which, unlike the prior art, is not designed to specifically reject entrained liquids, instead utilizing vaporization to provide a single-phase sample via the unique tube bundle power configuration. Accordingly, unlike prior art systems, the present system is designed to be fully compliant with BLM order 5 Facility Measurement Points (FMP).

To prevent sample distortion after the probe, the capillary passage with associated higher velocity following the linear-slot sampling probe of the present invention does not allow the two-phased sample to disassociate before it is vaporized by the novel and unique modular vaporizing regulator. These components are preferably located inside a unique housing/enclosure that facilitates 100% access to all components. The present housing/enclosure accomplishes this objective without any hinges or diagonal cuts. The system is designed so that the enclosure is independent of the probe and the components. The enclosure can be easily and completely removed without disturbing the probe or any other components of the system, while protecting the components and decreasing heat loss.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 5A is an isometric, front view of the probe tip illustrating the linear slot formed along the length of the body, and threaded connection end with outflow passage.

FIG. 5B is a greyscale view of the probe tip of FIG. 5A.

FIG. 6A is a bottom, partially cutaway view of the probe tip.

FIG. 6B is a side, partially cut-away, partially cross sectional, detailed view of the probe tip.

FIG. 6C is a side, partially cut-away, partially cross sectional, detailed view of the threaded end of the probe tip and outflow passage of FIG. 6B.

FIG. 7D is a side, partially cut-away view of the probe of the present invention extending into a pipeline, the probe having the modular conditioning system of the present invention mounted thereto, and illustrating the capillary passage 62 from the probe tip outlet 54 to the vaporizing regulator inlet 7.

FIG. 8A is a first side, perspective view of a tube bundle configuration with cover and insulation as utilized in the tube bundle interface for the present invention.

FIG. 8B is an end view of the tube bundle configuration with cover and insulation of FIG. 8A.

FIG. 8C is a second side, perspective view of the tube bundle configuration with cover of 8A.

FIG. 23A is an isometric, partial, cut-away view of the invention of FIG. 23, illustrating in detail opposing extensions 44', 44" forming radiant heat sink 44 which is formed to conduct heat from bottom cap 38 to provide radiant heat 60', 60" from extensions 44', 44", respectively, forming a heated area H therebetween to heat capillary tube 45 situated therein.

FIG. 23B is a side, partial, cut-away view of the invention of FIG. 23A, illustrating the migration of heat generated by heat block 37, the heat conducted 59 via raised center area 38' to vaporizer bottom cap 38, which heats vaporization chamber, and heat pipe 46 providing "moveable" heat transfer 61 from bottom cap 38, through vaporization chamber, to vaporizer bottom 42.

FIG. 24A is a front view of the first embodiment of the present invention in a modular sample system enclosure with one enclosure half removed.

FIG. 24B is a side view of the invention of FIG. 24A.

FIG. 27A is a front view of the adaptation of the GENIE brand JTR to a modular vaporizing regulator of the present invention.

FIG. 27B is a side view of the invention of FIG. 27A.

FIG. 28A is a section view of the invention of FIG. 27A.

FIG. 28B is a section view of the invention of FIG. 27B.

DETAILED DISCUSSION OF THE INVENTION

Figure 1:
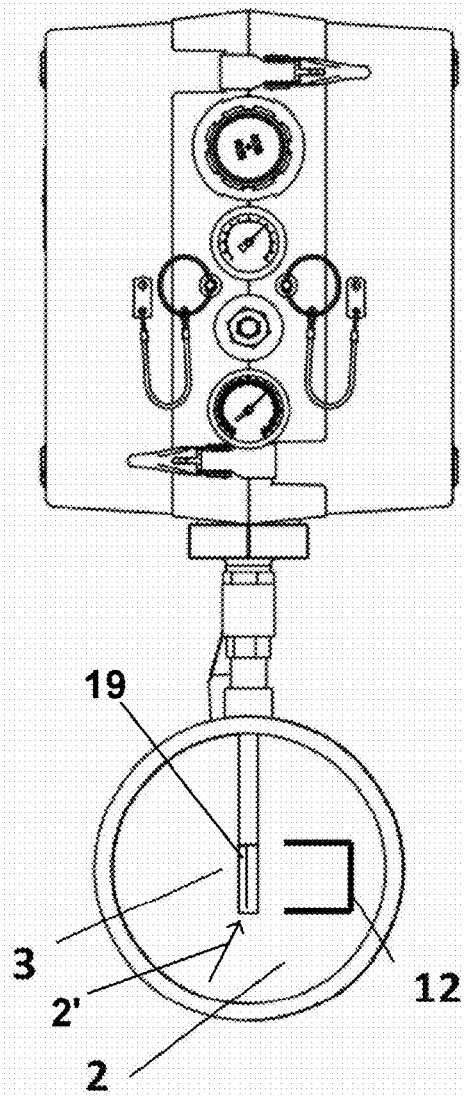
FIG. 1 is a frontal view of a sample conditioning system comprising modular sampling and/or conditioning components mounted to a substrate bracket, enclosed via a housing/enclosure 10 further showing an end view of the source of gas with entrained liquids, a linear sampling probe of the present invention situated therein, providing a passage to the modular sampling/conditioning components via substrate coupling.
Figure 2:
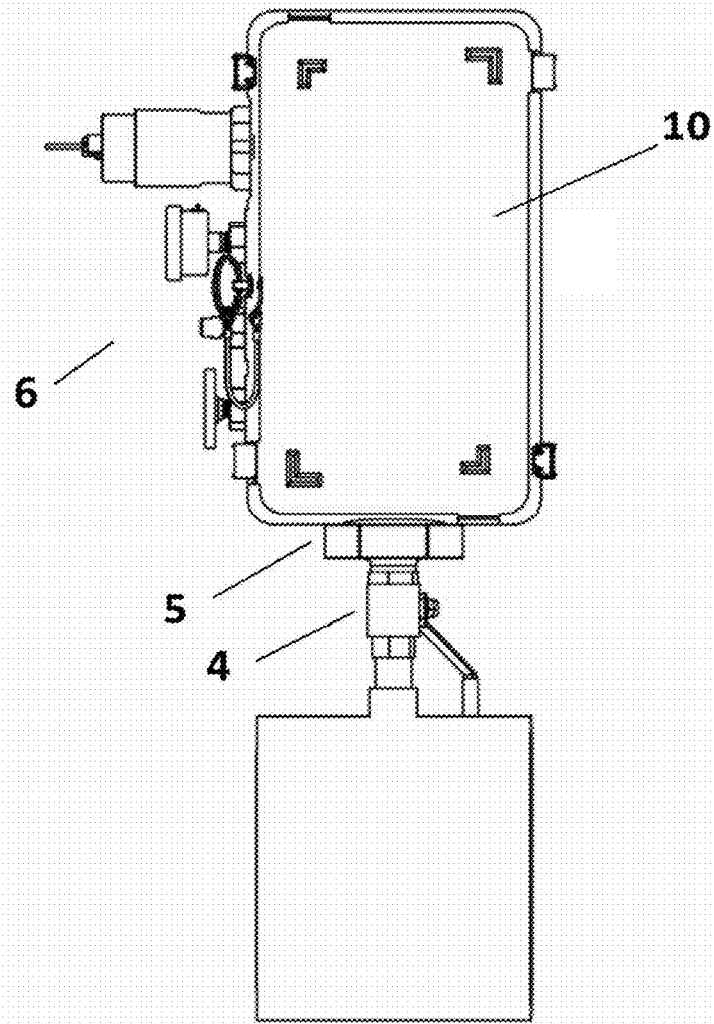
FIG. 2 is a side view of the invention of FIG. 1, with housing/enclosure 10 and substrate coupling 5 shown.

Referring to FIGS. 1-24B, the linear sample probe extracts a representative sample from the pipeline and transports that sample to the unique and innovative modular vaporizing regulator system of the present invention. The output of the modular vaporizing regulator yields a single phase gas only sample that leaves the modular sample conditioning system, where it is transported via a heated tube bundle to an analyzer for analysis.

Linear Sample Probe and Method of Sampling

Preferably, the preferred embodiment of the modular sample conditioning system of the present invention is mounted at the source of the sample, in this case a pipeline having pressurized process gas with entrained liquids.

FIGS. 1-4 show the pressurized source of gas (a/k/a process source) with entrained liquids 2 with insertion probe 1 having mounted thereto a linear, slotted sampling probe tip 3 positioned in the fluid stream so that the collection slot 19 of probe tip 3 faces the fluid flow, the probe tip 3 being positionable within the pipe in the center-third area to sample the center-third 12 as required (such as in certain BLM locations) to collect from the medial area of the flow stream, although the probe length and associated collection area can be modified as required. A probe isolation valve 4 is provided to selectively open and close the flow to the modular sample conditioning system 10, as required.

Referring to FIGS. 1-7C, formed through the outer wall 18 of the body 15 of the linear sampling probe tip 3 is an elongated, continuous or uninterrupted slot or opening 19 having a length aligned with the longitudinal axis L of the body 15, the slot or opening 19 having a relatively narrow width 19', and ends 17, 17' penetrating the outer wall or surface of the body, the slot forming first and second side walls within the body forming an outer edge 20 and an inner edge 20' corresponding to its depth and providing a passage to the outflow passage 21 having a small inside diameter.

In the preferred embodiment of the invention shown in the figures, the slot 19 preferably has a relatively uniform width preferably corresponding to, or less than, that of opening, while providing passage about to the longitudinal body at the inner edge 20' of the slot, shown about halfway through body. The slot as shown is aligned with and runs along longitudinal axis, although the length and position of the slot can vary depending upon the application.

As shown, the slot 19 in the exemplary, preferred embodiment of the probe tip of the present invention runs from just below the first 17 end of body 15 to about the second end 17' of body 15, with the inner edge 20' of the slot 19 engaging outflow passage 21 having a small inside diameter, as shown, which is formed to engage, as required, insertion probe 1 to provide a channel of flow of fluid therefrom, the outflow passage 21 in the present embodiment preferably having an inner diameter preferably equal to or less than the width of slot.

Figure 3:
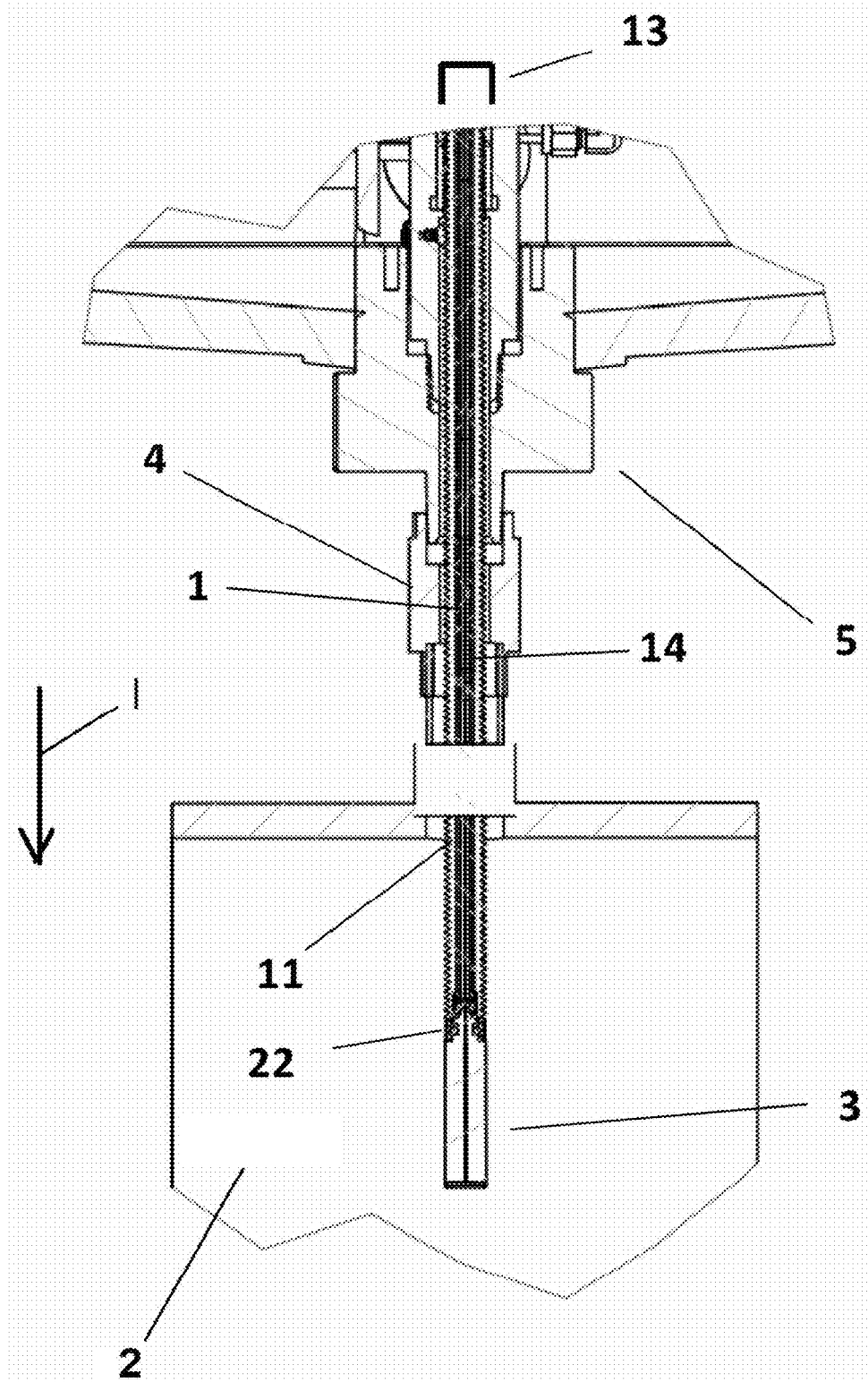
FIG. 3 is a partial, close-up view of the probe, housing/enclosure and substrate of FIG. 2.
Figure 4:
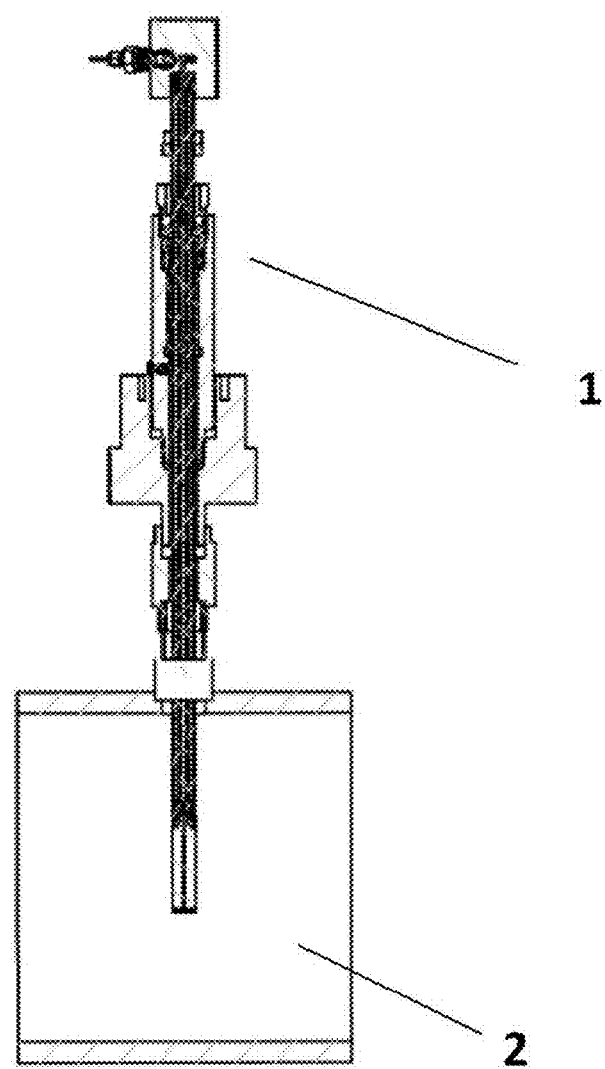
FIG. 4 is a side, sectional, cut-away view showing the insertion mechanism supporting the probe tip.
Figure 7A:
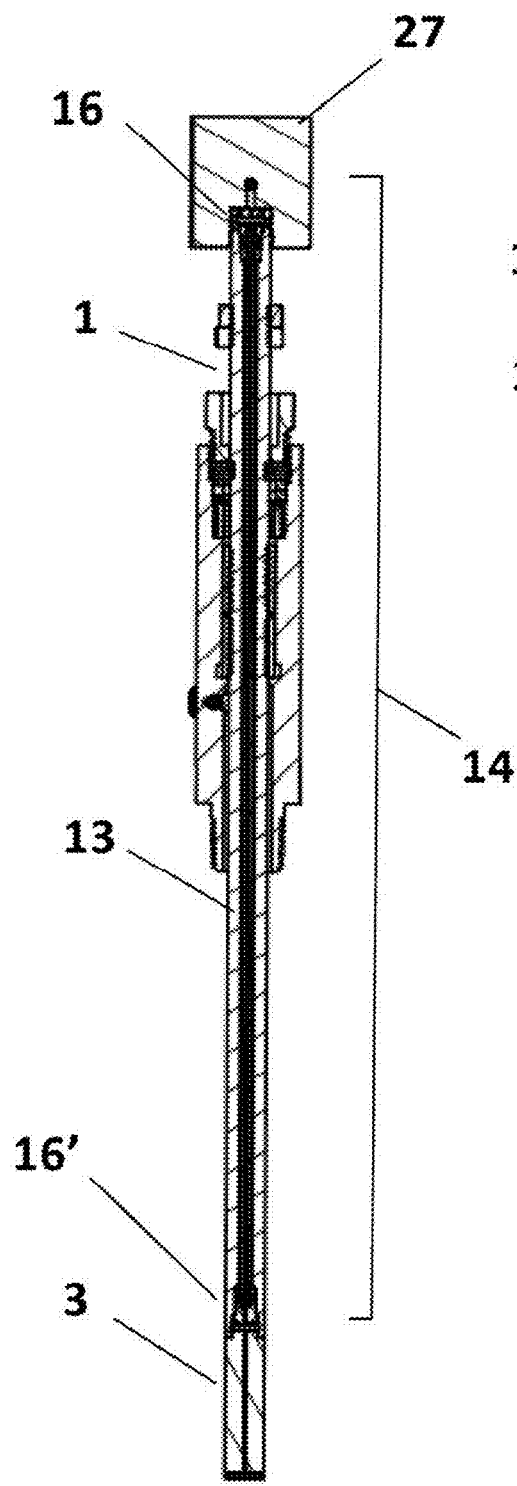
FIG. 7A illustrates a side, partially cut-away, partially cross-sectional view of the probe with slotted probe tip of the present invention having the capillary line through the length of the probe via probe passage, passing through the probe first end, rack, and the second end to probe tip.
Figure 7B:
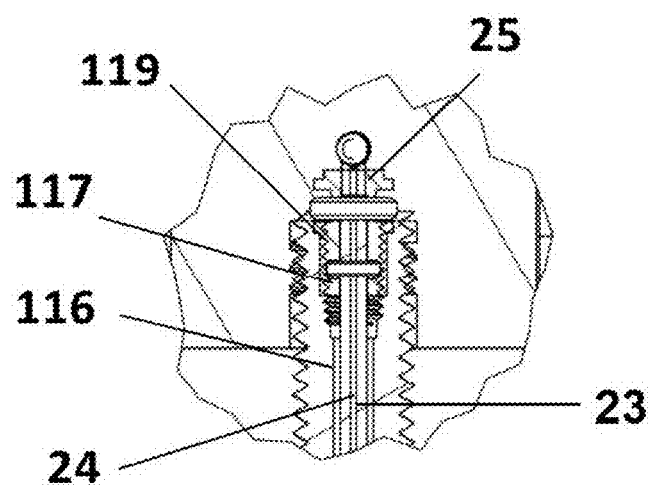
FIG. 7B is a side, partially cut-away, detailed view of the first end of the capillary tube engaging a flow component for flow out of the probe, sealed via o-ring.
Figure 7C:
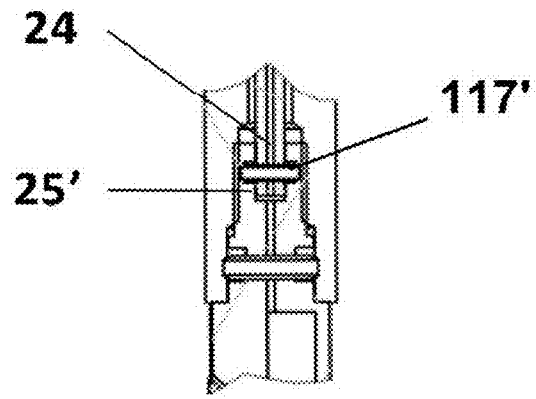
FIG. 7C is a side, partially cut-away, detailed view of the second end of the capillary tube engaging a flow component for flow out of the probe, sealed via o-ring.

The present system is formed to collect via the slot in the slotted probe tip a "linear sample" spanning a pre-determined area for sampling of the pipe, in the preferred embodiment of the present invention, the center-third area 12 of the flow as is illustrated in FIG. 3, or (in other versions) alternatively other zones or even the full span of the pipe from side-wall to side-wall, providing a representative sample of the fluid stream wherein a fluid sample of the fluid stream is collected along a line spanning the inner diameter of said pipe, even where there is present entrained liquid particles and even flowing liquid droplets/streams along the lower and/or upper surfaces of the pipe. While the present figures illustrate the position of the probe tip as vertical, this is not intended to be limiting, as the probe can be oriented at any angle relative the pipe, as long as the probe interface (insertion point) allows it.

The slot and outflow passage are preferably relatively narrow (less than 1/32" depending on the volume of fluid being sample, the speed, viscosity, and other factors) to remove a very thin slice of the total breadth of the fluid stream, so as to provide an accurate composite of the total fluid flow using principals similar to the integral principle as used in calculus.

As described, the body 15 has first 17 and second 17' ends defining a length therebetween, the slot 19 defining a narrow opening to a centrally disposed outflow passage 21 of preferably equal or less diameter than the slot width, thus providing the "integral slice" (in the present example, less than 1/32" wide slot from the outer surface of the probe) to intersect the small ID outflow passage (less than 1/32"), so that process fluid having sample gas containing entrained liquid 2 (FIG. 1) passes into the slot 19, passing therethrough to outflow passage 21 to the probe 1, at an equal or higher velocity than the fluid stream, so as to preserve the composition of the fluid stream and prevent disassociation of same.

The threaded end 22 of slotted probe tip 3 threadingly engages the second end of probe 1. Probe 1 has a passage 11 formed therethrough along its length, the probe 1 having an outer diameter 13 formed to allow its length to pass through probe isolation valve 4 (while in an open position) for selective insertion of the probe tip through isolation valve 4, and into the fluid stream.

The probe has formed therethrough along its length probe passage 11 to provide for the passage of fluid from the probe tip 3 there through. In the preferred embodiment of the present invention, a capillary tube 24 (in the present embodiment, formed of stainless steel) is provided having a length and first 25 and second ends 25' and is situated through the length of probe passage 11, the second end 25' of capillary tube 24 formed to engage the outflow passage 21 of probe tip 3 at a receiver 26 (having ID 21') formed within the threaded end 22 of probe tip 3, the first end 25 of capillary tube 24 sealingly engaging the probe tip's outflow passage 21 via o-ring 117'.

The second end 16' of insertion probe 1 engages the probe tip 3 via o-ring providing a sealed connection.

The capillary tube 24 in the present embodiment passes through the length of probe passage 11, the o-ring at first end 25 of capillary tube engaging a flow component 27 (in this case, a 90-degree angle connector), and is sealed via O-ring 117 and positioned to align with a capillary flow passage 119 for flow to the conditioning components downstream, in the present case, the flow would run from capillary tube to regulator inlet (7—FIG. 23), where any entrained liquid in the flow is vaporized by a heated regulator or vaporizer.

The capillary tube 24, like the probe tip 3 has an ID 23 formed to facilitate capillary tube capillary flow properties in the fluid flowing therethrough, which, in the present case, for wet gas (natural gas having entrained liquid) has been found to exist in a passage having an inner diameter of less than 1/32", although this figure could vary depending upon the surface tension of the liquids and other factors, further, the geometry of the capillary tube passage facilitate the flow of fluid therethrough at least at the velocity of the fluid stream from which the sample is taken, or at a higher velocity thereto.

In the present exemplary embodiment of the invention, the capillary tube 24 comprises Dursan 1/8" OD stainless steel tubing, which is situated inside the probe passage (and rack), and the present tubing having a 0.030" or less ID 23 to prevent sample disassociation via capillary action (and maintaining or providing enhanced fluid velocity), the optimal diameter of which can vary significantly depending upon the operational criteria and "wet gas" composition.

In the system of the present invention, it is imperative that no disassociation takes place in the sample fluid flow, from the moment the sampling occurs at the slotted probe tip, through the length of probe 1 (in the preferred embodiment, via capillary tube 24), to regulator inlet 7 (where the sample is conditioned via heated regulator and vaporized).

In the alternative to a capillary tube 24, the inner diameter (ID) of probe passage 11 itself could have an ID 116 formed to maintain or increase flow velocity from the probe tip along its length, and accordingly have an ID equal to or less than the width of the opening forming the slot 19 in the slotted probe tip 3 or ID of the outflow passage 23 (i.e., less than 1/32"), the geometry formed to provide capillary action in the wet gas flowing therethrough to prevent disassociation thereof.

Continuing with FIGS. 6A-6B, the slotted probe tip 3 of the present invention can include on the back side opposite slot opening 19 threaded apertures 28 formed to threadingly receive screws or other fasteners to facilitate the attachment of a cylindrical solids filter screen (for example, 40×40 mesh, 0.010" wire), to envelope the outer diameter (OD) 13 of the probe tip and prevent solids from entering the opening to slot 19, but large enough for the velocity of the sample to keep fluids from accumulating. A bottom screen disc D may also be provided at the second end 17' of slotted probe tip 3 held in place with a spiral retaining ring D'.

The system of the present invention ensures that the representative sample taken either in spot, batch or continuous fashion is not allowed to disassociate by providing the very small internal cavity forming the outflow passage, to maintain or enhance the fluid flow velocity through the system. The pipeline area is very large compared to the probe's very small interior and because of this vast difference, fluid in the outflow passage from the slotted probe tip to the probe will always be flowing at a higher velocity than the pipeline fluid.

The high gas velocity (higher than the source velocity of the pipeline) of the very small internal cavity/fluid outflow passage is formed to sweep all of the liquid particles at the same velocity as the gas particles being transported from the source to the probe. Therefore, it would remain "associated" with the gas from which it condensed, as verified from Applicant's own empirical testing. High velocity gas in the small internal diameter bore forming outflow passage engaging the relatively narrow slot of the probe will prevent any significant layer of liquid from accumulating on the surfaces. Even if an ultra-thin layer were to coat the probe's interior, the total area is anticipated to be small so that the impact would be expected to be negligible.

Continuing with FIGS. 1-7C, 10, and 24A-B, as shown, the slotted probe tip 3 of the preferred embodiment of the present invention is engaged to the capillary tube 24 (when utilized) then the end of an insertion probe 1, which then is lowered or inserted (e.g., via the rack in the preferred embodiment) into a pipeline, as may be required for certain BLM locations, the probe tip 3 positioned in the medial or center-third area 12 of the pipe with the opening forming the entrance of the slot 19 facing the flow stream 2'. While the present illustration shows the sampling position of the probe such that the probe tip 3 is in the center-third area 12 for BLM compliance, it is noted that the probe tip can be positioned elsewhere as required.

A portion of the fluid stream comprising a "linear slice" of the fluid flow in the positioned portion of the pipe then passes into the opening, into and through the slot, then through the pressure of the flow stream is urged through the outflow passage, capillary tube with capillary flow on to the modular conditioning components for heating and/or collection, online analysis, monitoring, or other usage. As earlier indicated outflow passage in the preferred embodiment as well as downstream the probe tip to the conditioning components preferably has an inner diameter commensurate with the width of the slot formed in the body forming the slotted probe tip, resulting lesser area than the slot, so as to facilitate at least equal but more likely greater fluid velocity flow through said outflow passage, to keep the fluid from slowing and possibly disassociating.

Along with the higher velocity sweeping the wet gas sample so that it does not disassociate, conventional science recognizes that, as the inside diameter or cross-sectional area of a slot or passage decreases, a static liquid having sufficient surface tension will interact with the walls of sufficiently small slot or passage to trigger static capillary functionality, a phenomenon known to occur when the static liquids adhesion to the walls is stronger than the cohesive forces between the liquid's molecules. Such a phenomenon, in combination with the higher velocity sweep, is believed to be an inherently motivating feature in the present invention when wet natural gas passes through the slot or wall when the clearance is at most (depending on various factor) equal or preferably generally less than 1/32", although the exact threshold where static capillary function can and will occur in this dynamic sweeping combination can vary depending on the composition of the wet gas, as well as other factors.

In the probe of the preferred embodiment of the present invention, the slot as well as its flow passages therefrom are formed to have a very small internal cavity so as to facilitate capillary action which has been found to makes the slip ratio of the fluid composition flowing therethrough very nominal, essentially unity, so that, at the appropriate velocity the effect is to sweep all of the entrained liquid particles at the same velocity as the gas, so as to prevent disassociation of same.

While the velocity of fluid flow through the slot and probe passage is preferably higher than that of the fluid stream in the pipeline, and without reduction in velocity as it flows through the system to the conditioning component (such as the vaporizer as will be discussed herein), it is noted that with any larger inside diameter or clearance, (for example, larger than 1/32 inch, as with prior art probes with inside diameters of 1/4 inch or such), the two phases might disassociate even with the higher velocity flow. It is therefore important that the velocity and diameter size be balanced to exploit the capillary effect and prevent disassociation of the wet gas composition.

A wet gas composition can vary significantly depending upon its source, typically comprising a multicomponent hydrocarbon stream and realistically may comprise at least six different components in two phases. Also, the fluid may contain undesirable injected components such as glycols and scavengers. However, it is believed that a combination of phase diagram data and empirical testing can provide a guide to determine an optimal slot and flow passage geometry for a particular application. Accordingly, the applicant is unaware of any direct calculations for this combination effect of passage size and velocity, but in-house testing suggests the slot and internal passageway will be less than 1/32" in diameter, the optimal size depending on the wet gas composition and environmental criteria.

In the preferred embodiment of the present invention, the sample, once taken, is then directed to a modular vaporizing regulator to vaporize any liquids, providing a single-phase sample, then to a process analyzer, monitor, sample container, or other end use.

Considering the above and foregoing, a method of sampling a wet gas from a fluid stream the present invention could therefore comprise the steps of, for example:

a. providing a probe having a probe passage formed along its length having an inner diameter having a geometry to facilitate capillary action in wet gas flowing therethrough, at a higher velocity than said fluid stream;

b. allowing wet gas to flow from said fluid stream into and through said probe so as to provide capillary action at the higher velocity;

c. allowing said capillary action to prevent disassociation of said composition of said wet gas as it flows through said probe passage.

Still further, the method of sampling a wet gas comprising gas with entrained liquid in a fluid stream having a flow velocity could comprise, for example, the steps of:

a) providing a probe tip 3 engaging a probe 1, said probe tip comprising an elongated slot situated substantially along its length;

b) laterally positioning said probe tip in the fluid stream so that said slot faces the stream;

c) utilizing said slot to receive a linear sample of flow of said stream into said body, providing received flow;

d) flowing said received flow through a passage sized to have capillary flow properties to prevent disassociation; and vaporizing said received flow to provide a representative sample.

Still another method of the present invention can be summarized as follows:

i. analyzing the wet gas to provide compositional analysis—analysis can be accomplished via, for example, an analyzer A, which might comprise, for example, a gas chromatograph of mass spectrometer, or other analyzer known and utilized in the industry;

ii. utilizing said compositional analysis to determine, for example via the Poiseuille Equation as discussed supra, the dimensions required in a passage to facilitate capillary action in the flow of said wet gas therethrough, providing a capillary passage geometry, which in the case of a radial passage might comprise an internal diameter, for example.

iii. providing in a probe and passage connected to said probe having said capillary passage geometry;

iv. inserting I said probe into said fluid stream;

v. allowing wet gas to flow 2' from said fluid stream into and through said probe passage and outflow passage to a conditioning component such as, for example, a vaporizing regulator as discussed herein;

vi. utilizing the flow of said wet gas through said capillary passage geometry to facilitate capillary action in said wet gas flowing therethrough;

vii. utilizing said capillary action to prevent disassociation of said composition of said wet gas as it flows therethrough.

As discussed, optimally said probe passage has an outflow passage engaging said elongated slot, which outflow passage is sized in relation to said slot so as to facilitate the flow of fluid therethrough at least at the flow velocity of fluid flowing through said slot;

As discussed, to be compliant with present BLM regulations at FMPs, preferably the probe tip 3) would be situated in the center third (medial area) of the flow.

While less than 1/32" is indicated as an example of the diameter for capillary flow in the present wet gas application, it is reiterated that the optimal specific geometry can vary depending on a number of criteria. A combination of phase diagram data and empirical testing could be used as a guide to determine the optimum capillary diameter/geometry for the particular wet gas composition, taking further into account the particular pipeline/flow property, application, environmental, and other factors.

Tube Bundle and Boot

Figure 9:
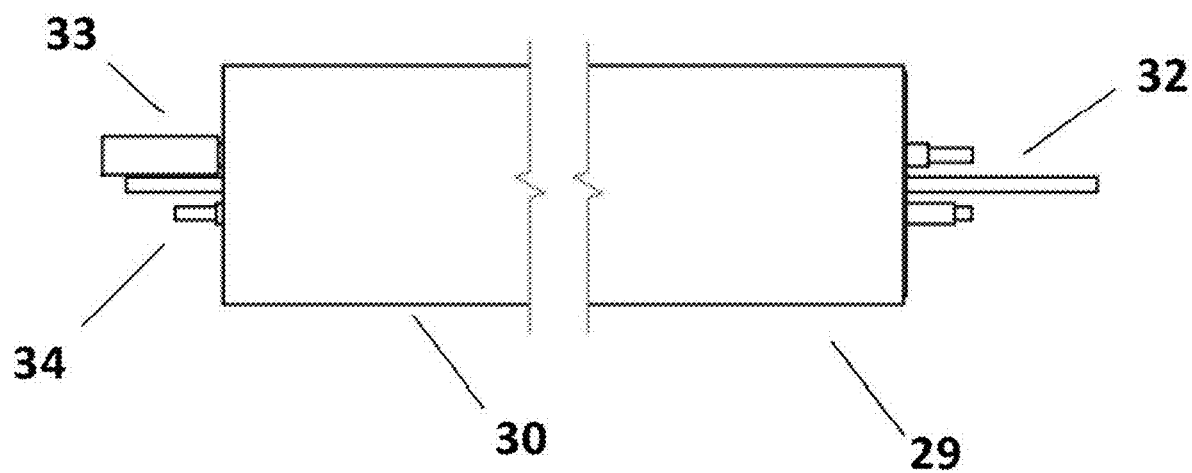
FIG. 9 is a side view of the invention of FIG. 8A illustrating a length of tube bundle showing a terminated end and components including sample tube and power cord.

FIGS. 8A-9 shows the power conductor or cord 34 of the present invention integrated into the tube bundle 29. Companies such as Thermon Manufacturing Company, www.thermon.com, offer custom tubing bundle options for their products, which might include non-heated auxiliary conductors within tube bundle, as denoted in their Application Flyer PAF0027-0714 (form PAF0027-0714).

Said figures further show the tube bundle 29 protected along its length via cover 30, and having insulation 31 therethrough to isolate the components as desired. Situated along the length of the tube bundle is sample tube 32 for conveying sample fluid from the modular sample conditioning system, the sample tube in the present preferred embodiment comprising a 1/8" OD Stainless Steel tube that is heated by an adjacent heat trace 33 along the length of the tube bundle 29, the heat trace 33 terminating at the end of tube bundle.

In the present invention, a separate, non-heated power cord 34 of adequate gauge to convey the total required power to the unique sample conditioning system or other apparatus (for the length required) is provided in the tube bundle 29.

Figure 14:
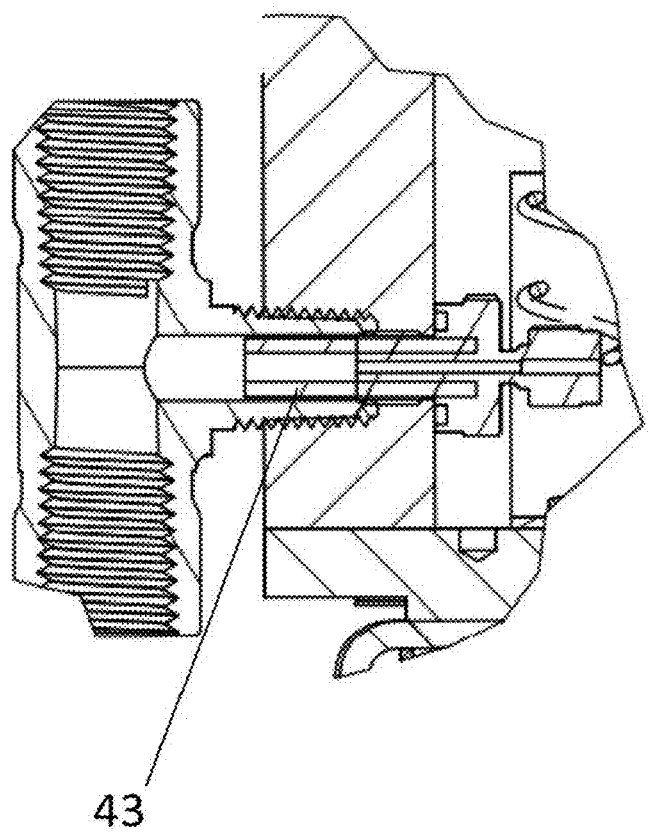
FIG. 14 is a partial, close-up view of FIG. 13, illustrating the thermal isolation barrier of the present invention, to prevent partial fractionization of the liquid sample.
Figure 15:
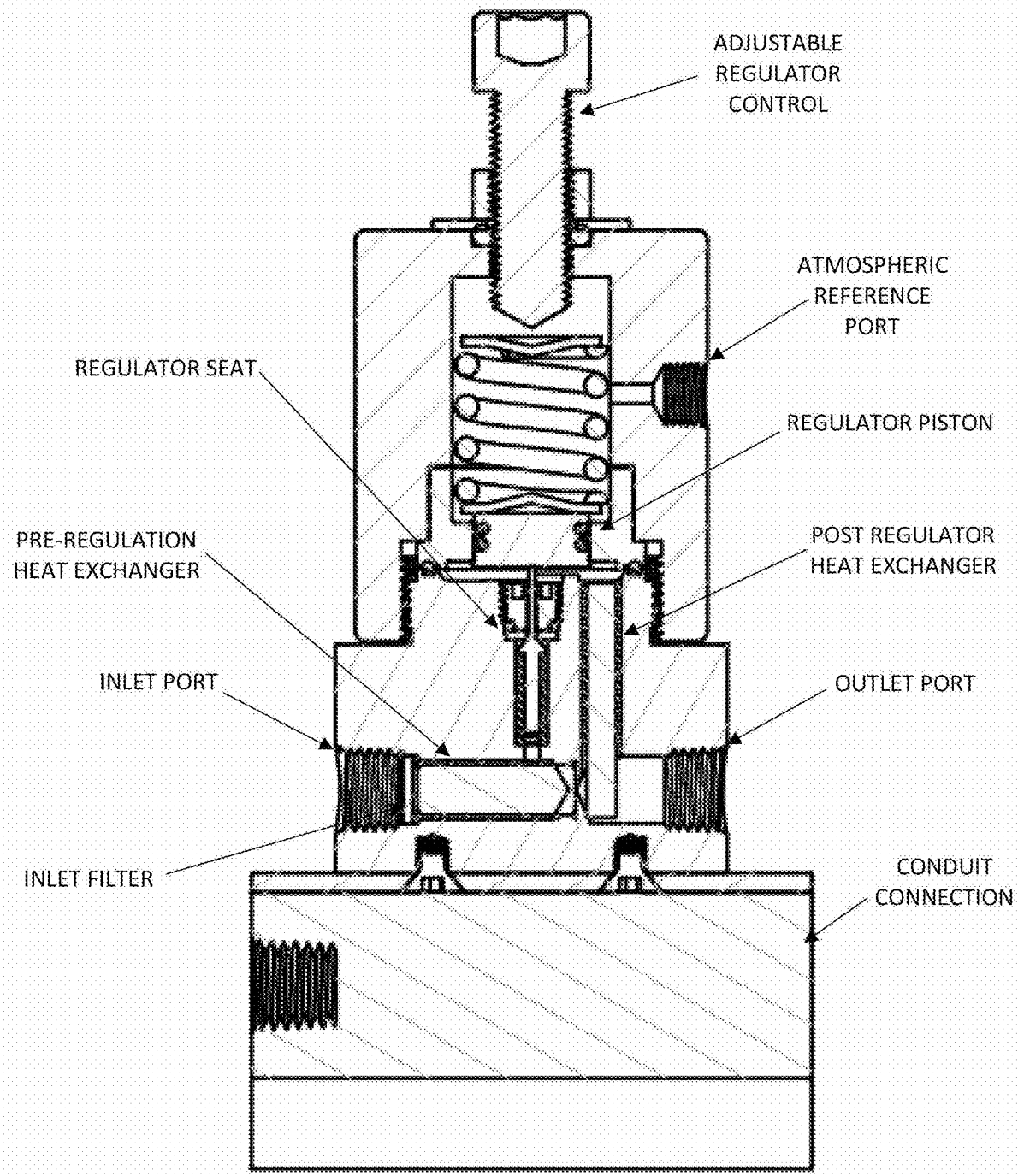
FIG. 15 is a color section view of the applicant assignee's prior art GENIE brand Heated Regulator (GHR) with pre and post heat exchange.

The length of tube bundle 29 can vary depending on the power source location and the sample system location. FIG. 14 is a grayscale drawing of FIG. 12. Rather than using power from the heat trace which normally would provide inadequate power for vaporizers or the like, the present invention provides the separate power conductor or cord 34 in the tube bundle for utilization as the power source. The power cord 34 may bring 110V AC or 24V DC to the modular sample system (and power heater block 37) utilizing the tube bundle, and again, its gauge may vary depending on its length and power requirements of the system.

Figure 10:
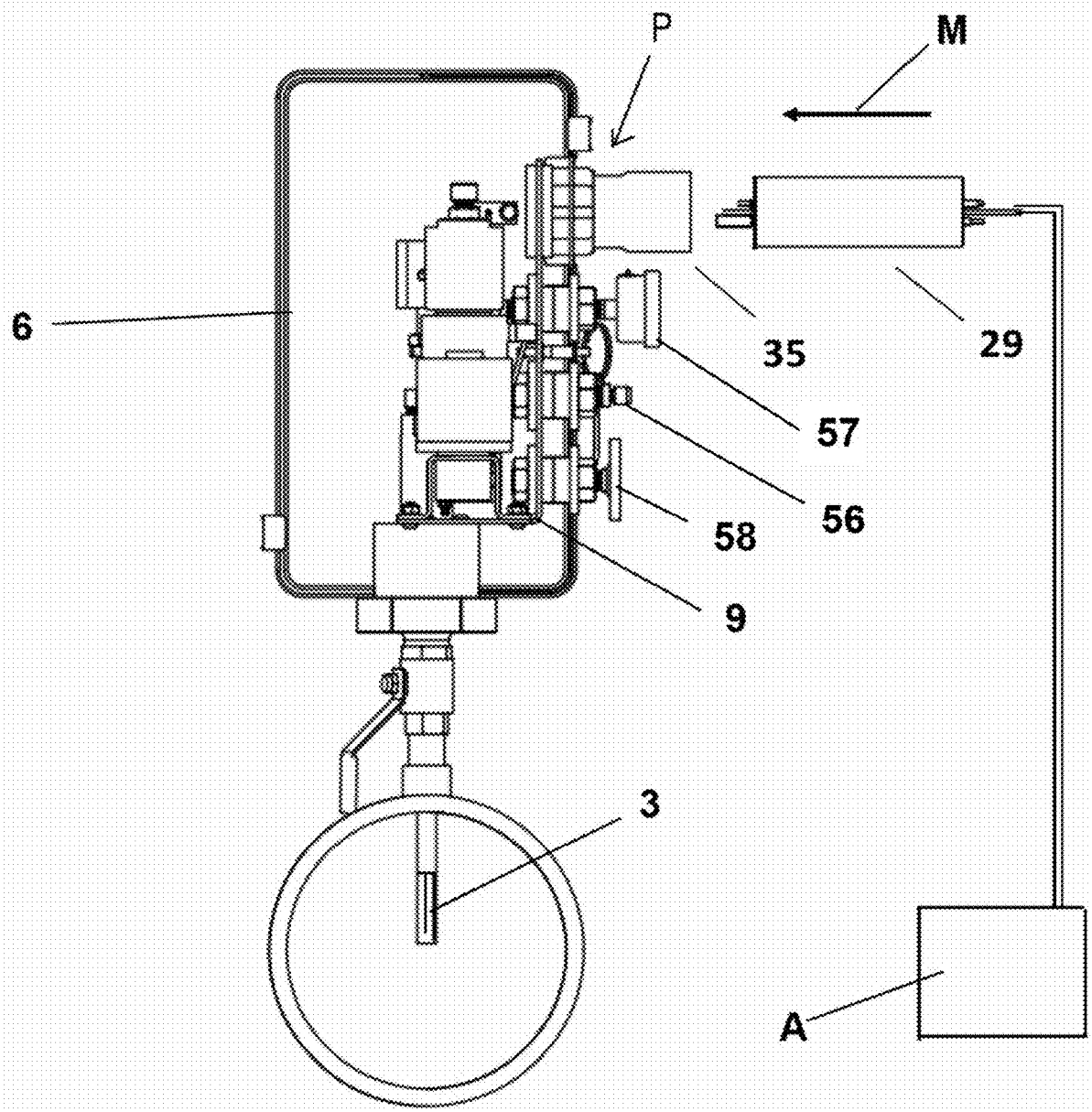
FIG. 10 is a side view further illustrating the insertion of the first end of tube bundle into tube bundle boot of the modular sample system, along with various modular sampling conditioner components including pressure gauge 57, relief valve 56, and temperature gauge 58.
Figure 11:
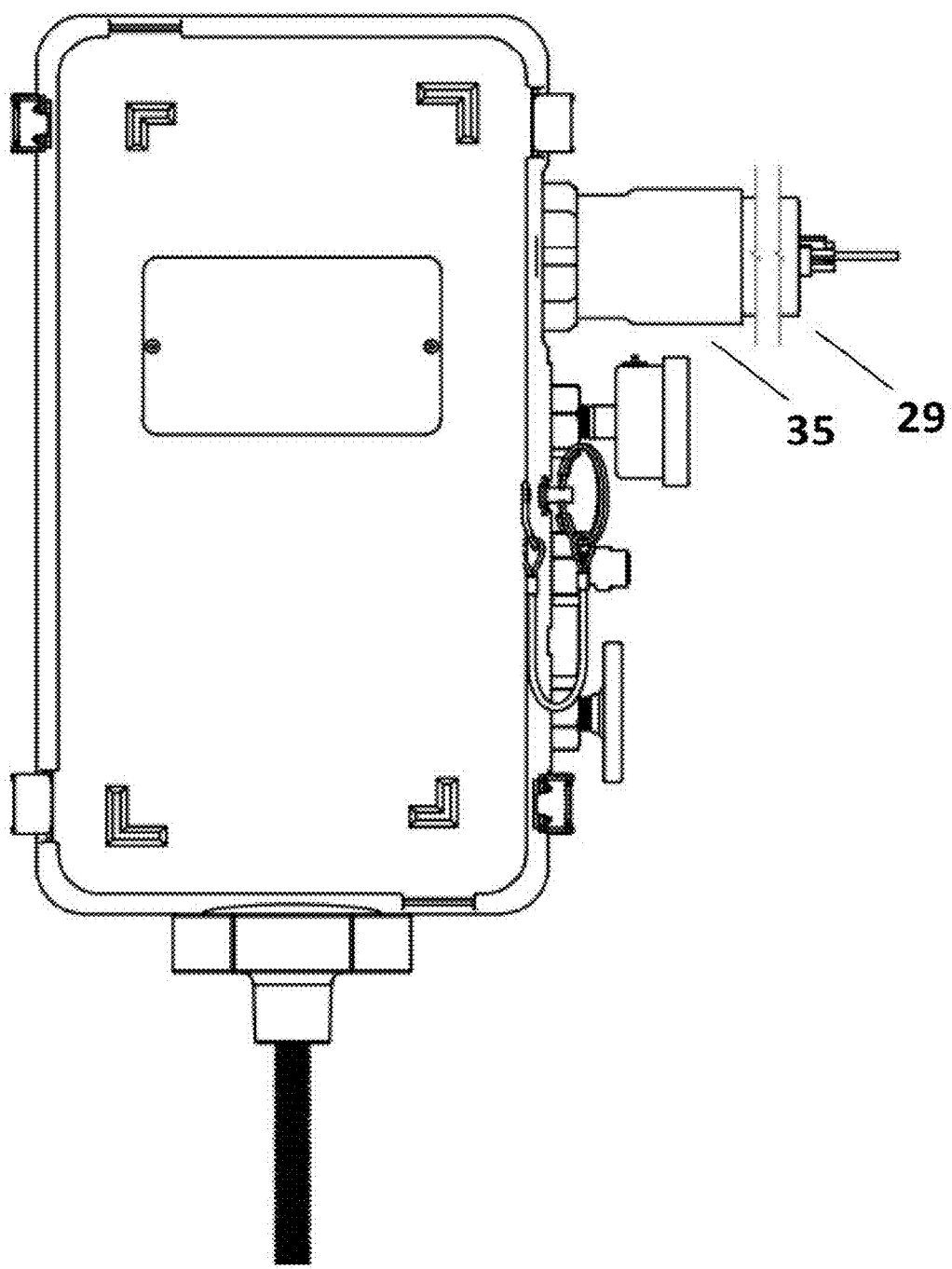
FIG. 11 is a side view of the modular sample system illustrating the first end of the tube bundle fully inserted and swaged in the tube bundle boot, with the power cord engaging the power cord receiver, and outlet tubing engaging the outlet tubing connection.
Figure 12:
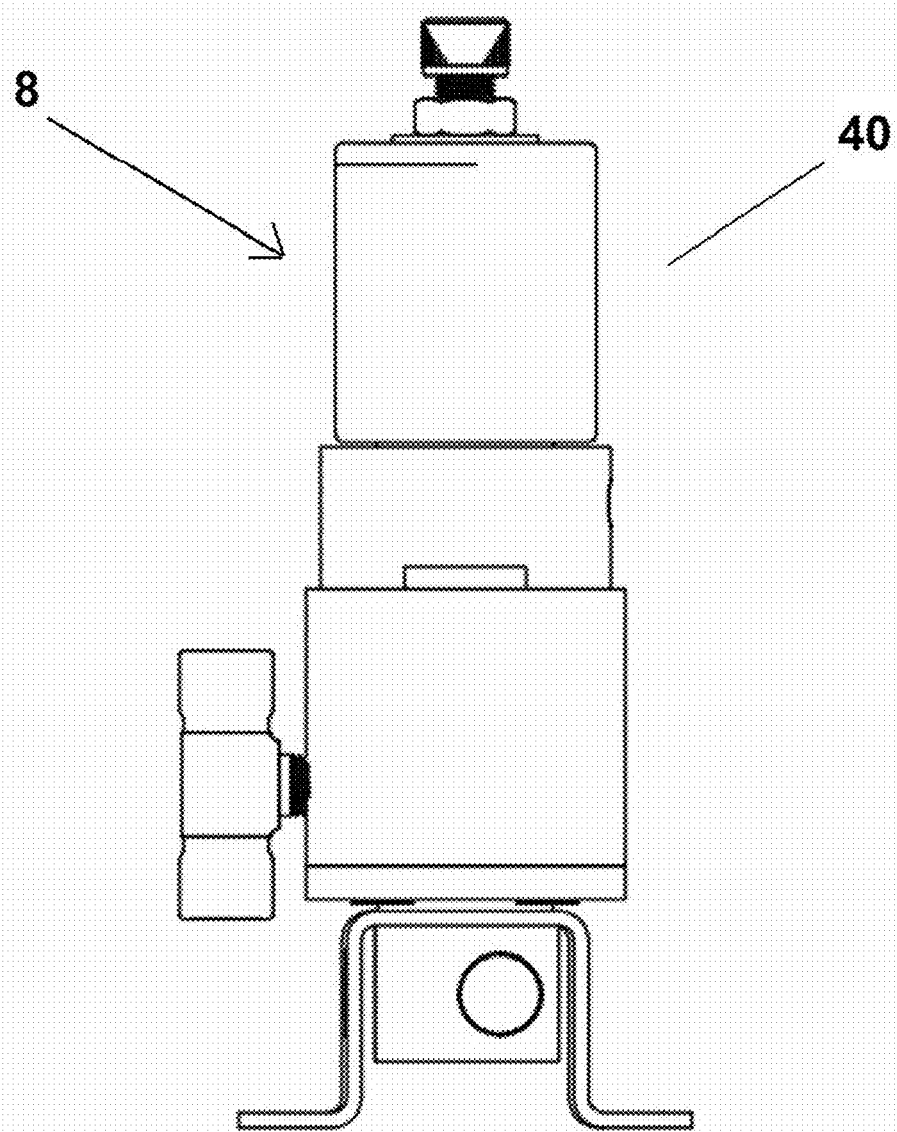
FIG. 12 is a side view of the second embodiment of the modular vaporizing regulator of the present invention.
Figure 13:
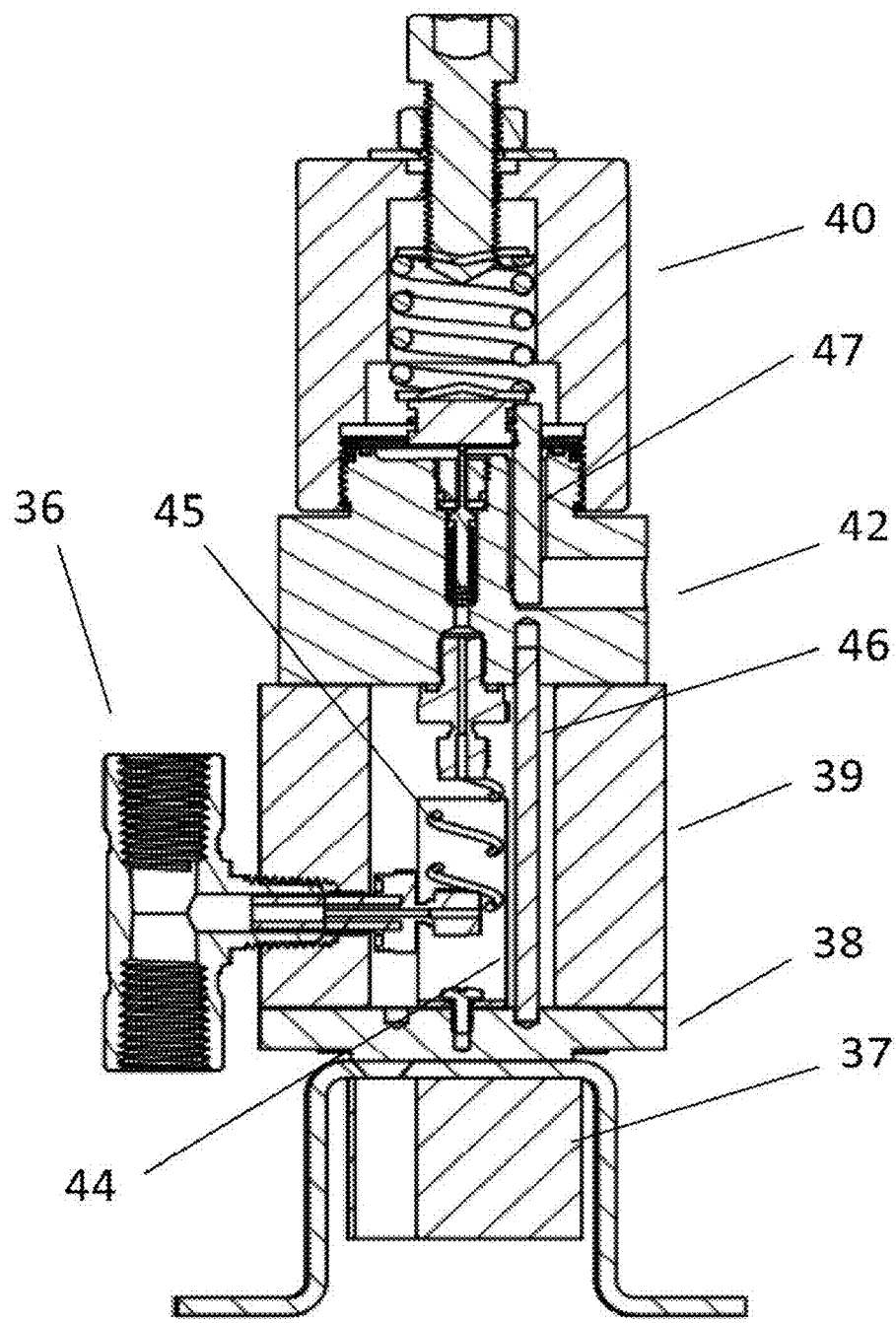
FIG. 13 is a section view of the invention of FIG. 12, further showing an internal view of the construction of the second embodiment of the present invention.

FIGS. 10-11 illustrates a tube bundle boot 35 mounted M to the bracket 9 of a modular sample system 6, the tube bundle boot 35 formed to receive the tube bundle 29. In addition, the tube bundle boot 35 is formed to allow power cord 34 to pass therethrough to engage a power cord receiver or the like in the modular sample system 6.

The sample tube 32 in tube bundle 29 is formed to extend therefrom and pass through tube bundle boot 35 so as to engage in sealed fashion and connect to, for example, a connection in the modular sample system.

Modular Vaporizing Regulator

In the preferred embodiment of the invention shown in the FIGS. 7A-7C, 10-11, 22-24, and 27-28, a modular vaporizing regulator 8 is mounted in the modular sample conditioning system 6 and receives a representative sample from the linear sample probe via slotted probe tip 3 or the like.

Figure 17:
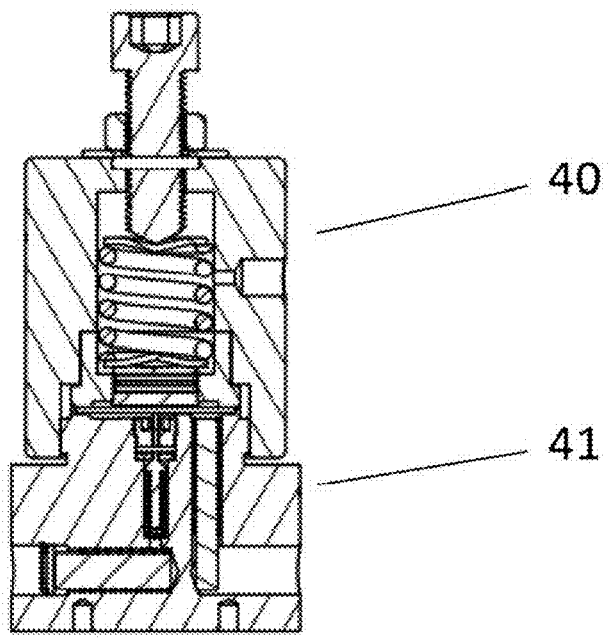
FIG. 17 is a section view of the prior art GENIE brand Heated Regulator (GHR) with the heater block and bracket removed.

The modular vaporizing regulator of the exemplary embodiment of the present invention (FIG. 23) comprises the GENIE brand Heated Regulator (GHR) component or top 40 (also referred to as the upper regulator module), with the GHR bottom section of FIG. 17 removed and replaced with a new and unique modular vaporizer bottom 42 (also referred to as a vaporizer/regulator interface module), the regulator top 40 and bottom 42 forming the regulator component, which in turn is stacked upon and mounted to the new modular vaporizer chamber 39 (also referred to as a vaporizer module), mounted to a bottom cap 38, as further described herein.

Figure 19:
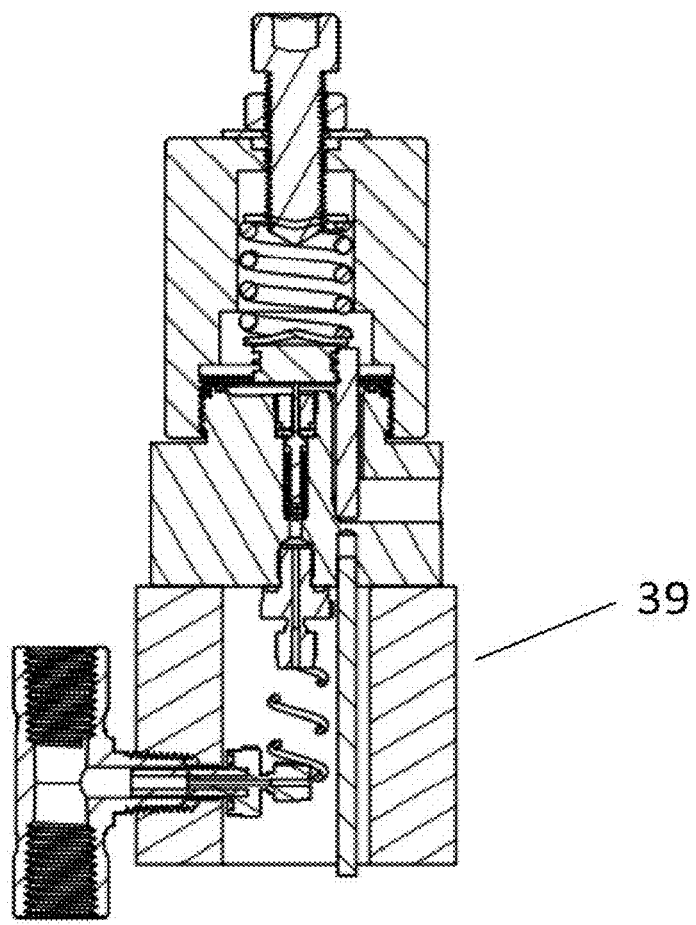
FIG. 19 is a section view of FIG. 18 with the modular vaporizer chamber of the present invention added.
Figure 20:
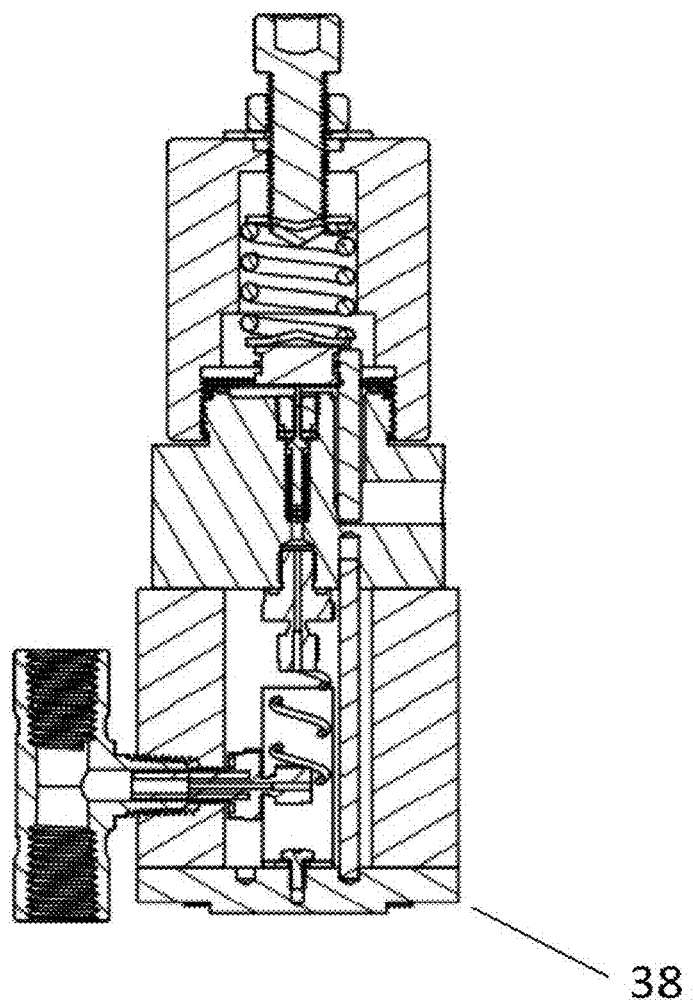
FIG. 20 is a section view of FIG. 19 with the modular vaporizer bottom cap added to the present invention.

FIG. 20 is a section view of FIG. 19 with the modular vaporizer bottom cap added to the present invention. The linear sample probe has an outlet passage with a small inside diameter. Small diameter capillary tubing 24 connects the outlet of the linear probe to the inlet 7 of the modular vaporizing regulator.

Figure 23:
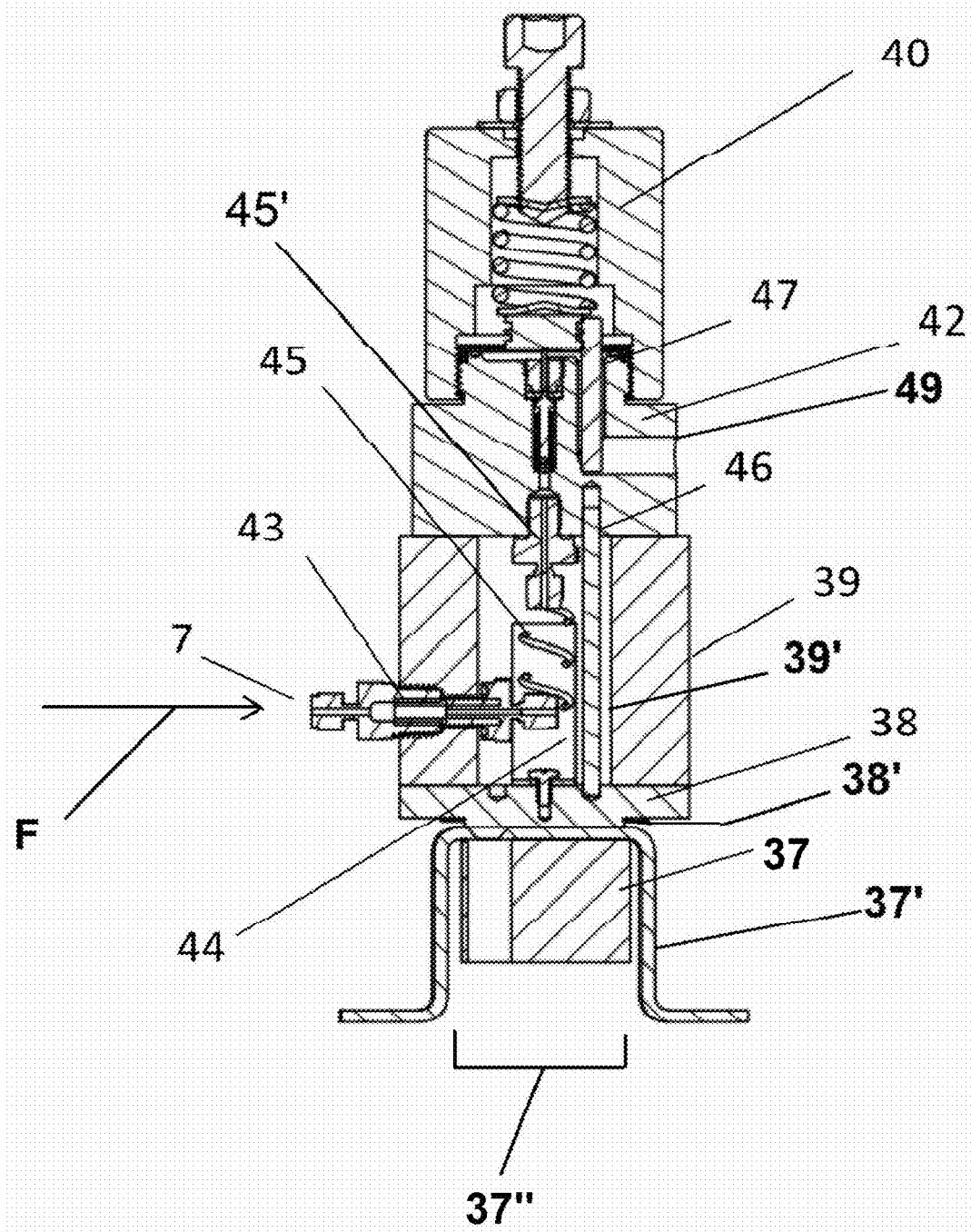
FIG. 23 is a section view of FIG. 22, further showing an internal view of the construction of the first embodiment of the present invention.

Continuing with FIGS. 23, 23A-B, the novel and unique modular vaporizing regulator utilizes three types of heat: conduction heat from a heater block 37, radiant heat from a heat sink 44, and moveable heat transfer from a heat pipe. Radiant heat sink 44 has emanating therefrom parallel opposing extensions 44', 44" forming radiant heat sink 44, said heat sink 44 formed to conduct heat from bottom cap 38 to provide radiant heat 60', 60" from extensions 44', 44", respectively, forming a heat zone H. The modular vaporizing regulator thermally engages a heater block 37 via mounting bracket 37' configured so that conduction heat passes from the heater block 37 to the modular vaporizer bottom cap 38. The vaporizer bottom cap 38, forming the base of the vaporizer section, has a raised portion 38' formed and oriented to fully engage/contact heater block and or bracket 37' (formed of heat conducting material) for maximum heat transfer, preferably in the center area of the bottom cap 38. Preferably, the raised portion 38' of bottom cap 38 has dimensions which generally correspond to inner diameter 39' of the modular vaporizer chamber 39 as well as the width 37" of the heater block 37.

Heat generated by heater block 37 is thereby transferred through bottom cap 38 to the modular vaporizing chamber 39. Inside vaporizing chamber 39 is a radiant heat sink 44 mounted to the modular vaporizing regulator bottom cap 38. Heat generated by heat block 37 is transferred via conduction through raised center area 38' to vaporizer bottom cap 38, which heats radiant heat sink 44 and vaporization chamber.

A heat pipe 46 thermally engages the modular vaporizing regulator bottom cap 38, the length of said heat pipe 46 passing thru vaporizing chamber 39, transferring heat to the modular vaporizing regulator bottom (42 in FIG. 23 or 48 in FIG. 28B) to provide heat so as to counteract any Joule-Thomson cooling effect which might occur due to pressure decline, the regulator bottom forming the outlet pressure drop area of the vaporizer. Heat pipe 46 thereby provides "moveable" heat transfer 61 from bottom cap 38, through vaporization chamber, to vaporizer bottom 42.

Figure 25:
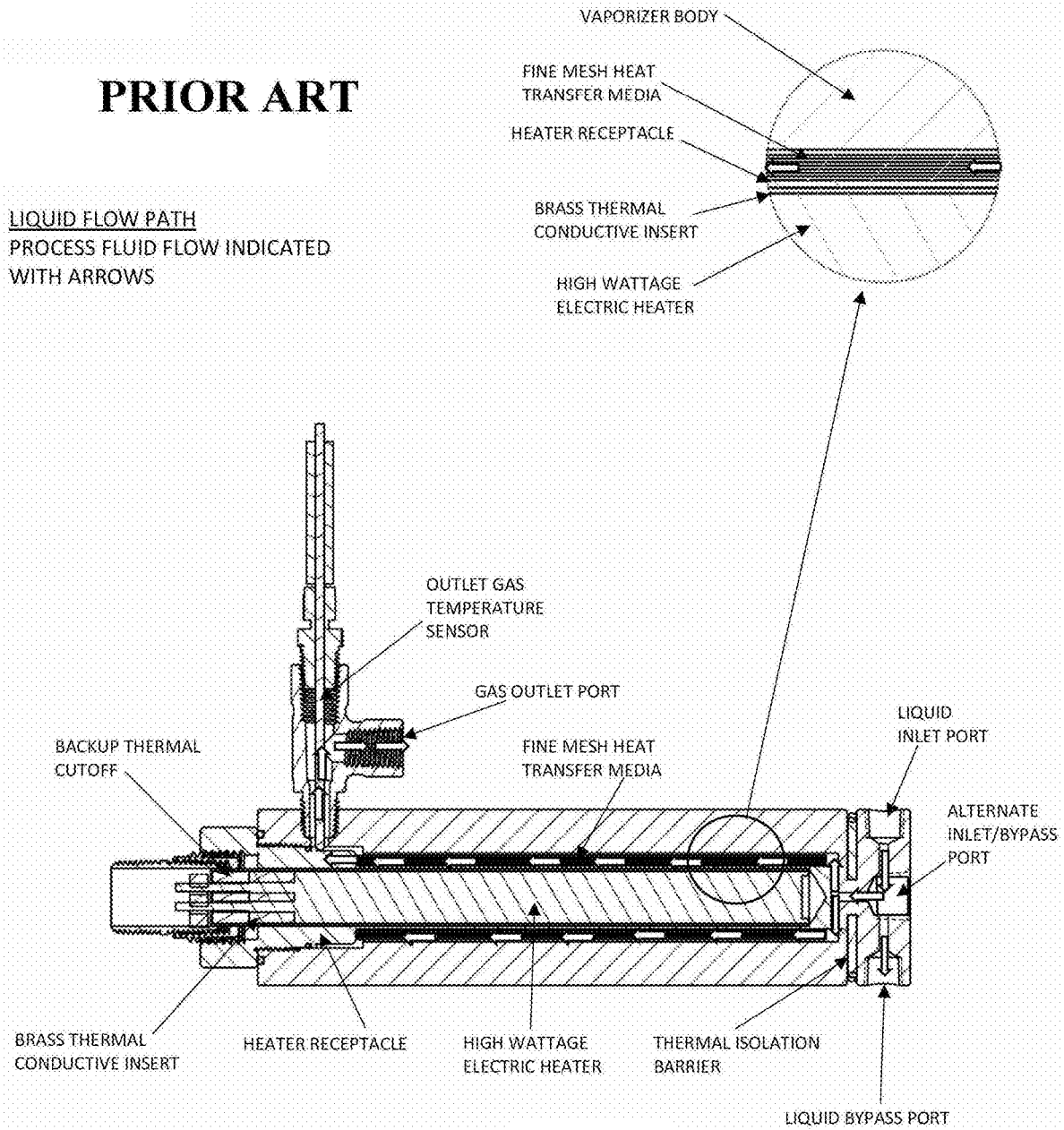
FIG. 25 is the applicant assignee's prior art vaporizer (GENIE brand Vaporizer).

Capillary tubing 45 (tubing sized internally to facilitate capillary action in the fluid flowing therethrough) is provided in the modular vaporizing chamber 39. The capillary tubing 45 (formed of stainless steel in the exemplary embodiment) connects the sample inlet (regulator inlet 7) with thermal isolation barrier 43 (as utilized in applicant assignee's prior art GENIE brand vaporizer FIG. 25) to the modular vaporizing regulator bottom (42 or 48). For example, a plastic tubing insert could be used as a thermal isolation barrier to resist heat from the vaporization chamber and thereby maintain a cold zone at the inlet so as to facilitate flash vaporization once the fluid flows into the capillary tubing in the vaporization chamber, as further described herein.

Capillary tube 45 runs through vaporization chamber in the heat zone H between radiant heat sink extensions 44', 44'', shown longitudinally aligned with same, the capillary tube preferably formed of metal or other heat conductive material, and preferably coiled in the area of heat zone Z to maximize heat transfer to the fluid flowing therethrough, so as to vaporize same.

Any entrained liquid flowing through capillary tubing 45 is flash vaporized without fractionation due to the thermal isolation barrier 43 (which might comprise, for example, a plastic PTFE tube encircling said capillary tube) to prevent heat from reaching the liquid until it is inside the vaporization chamber 39 via capillary action tube 45. The capillary tube ID is sufficiently small to prevent sample disassociation as it is vaporized within the heated zone of the modular vaporizing chamber 39. The optimal length and inside diameter of the capillary action tube 11 can be determined and adjusted according to the Poiseuille Equation as applied in fluid dynamics, which reads:

Volumetric Flow of Liquid=(delta P×tubing inside radius to the 4th)/(8/pi×viscosity×length)

Where:
delta P is the pressure difference between the ends of the tube

An exemplary application of the Poiseuille Equation in the present case might entail, for example:
Liquid Propane example:
Liquid propane viscosity=0.11 cP=0.0011 P
For tubing with an inside radius of 0.015 inches and a delta P of 10 psi that is 3 inches long, the volumetric flow rate would be approximately 2.4 cc/min of liquid propane.
Propane has a liquid to gas expansion ratio of 270:1. Therefore, one could expect approximately 640 cc/min of propane vapor.
In the present example, the vaporizer could have a 3-inch-long coil of 1/16 inch outside diameter stainless steel tubing with an inside diameter of 1/32 inch and have an output of 640 cc/min of propane vapor.
The tube may consist of lengths of different inside diameter tubing pieces connected together, although preferably the ID of the passage should preferably remain consistent at the connections.

Any liquid in the fluid stream in the capillary action tube 45 passing through heated modular vaporization chamber 39 during operation is vaporized due to the combined heat action of the heated radiant heat sink 44 as well as the heated regulator valve stem and seat, which are heated by heat pipe 46. The heated vapor then makes its way through the capillary action tube 45 to the outlet passing the post regulator heat exchanger 47, which is formed to transfer heat to the vaporizer outlet 49.

The exemplary capillary tube, being formed of stainless, a natural thermal conductor, transfers the heat from the vapor chamber to the fluid passing therethrough, vaporizing any entrained liquid(s) therein. The capillary tube is shown in the vaporization chamber in its preferable coiled configuration, which enhances performance by heating a longer section of the tubing within the vaporization chamber. The heated vapor then passes from through vaporizer outlet 45', through regulator 40 then makes its way out of the modular sample conditioning system via regulator outlet port 49 (FIG. 23) then through heated tube bundle to an analyzer A (FIG. 10) for analysis such as via gas chromatography, spectroscopy, or analyzer/analysis as used in the industry.

The modular vaporizing regulator of the exemplary embodiment of the present invention (FIGS. 23, 23A-23B) is unique in that there is provided a stackable vaporization regulator comprising three component sections which may change in size or operational criteria depending on the circumstances of use, the system providing the regulator top 40 and bottom 42 forming the regulator section, or the first component which is stacked upon the modular vaporization chamber 39. with regulator bottom 42 as shown enclosing one side of the chamber 39, and bottom cap 38 enclosing the other side of chamber 39, the enclosed vaporization chamber forming the second component. The bottom cap further is formed and oriented relative to the heater block and/or bracket so that raised area 38' fully receives heat via block heater 37 to transfer same, the heater component comprising the third component in the system.

In a second embodiment of the present invention (FIGS. 12-14 and 19-21), the inlet of the modular vaporizer chamber 39 is shown receiving fluid via a liquid bypass port 36. The bypass feature operates in similar fashion to that utilized in applicant assignee's prior art GENIE brand Vaporizer (FIG. 25), its contents incorporated herein by reference thereto.

Figure 26:
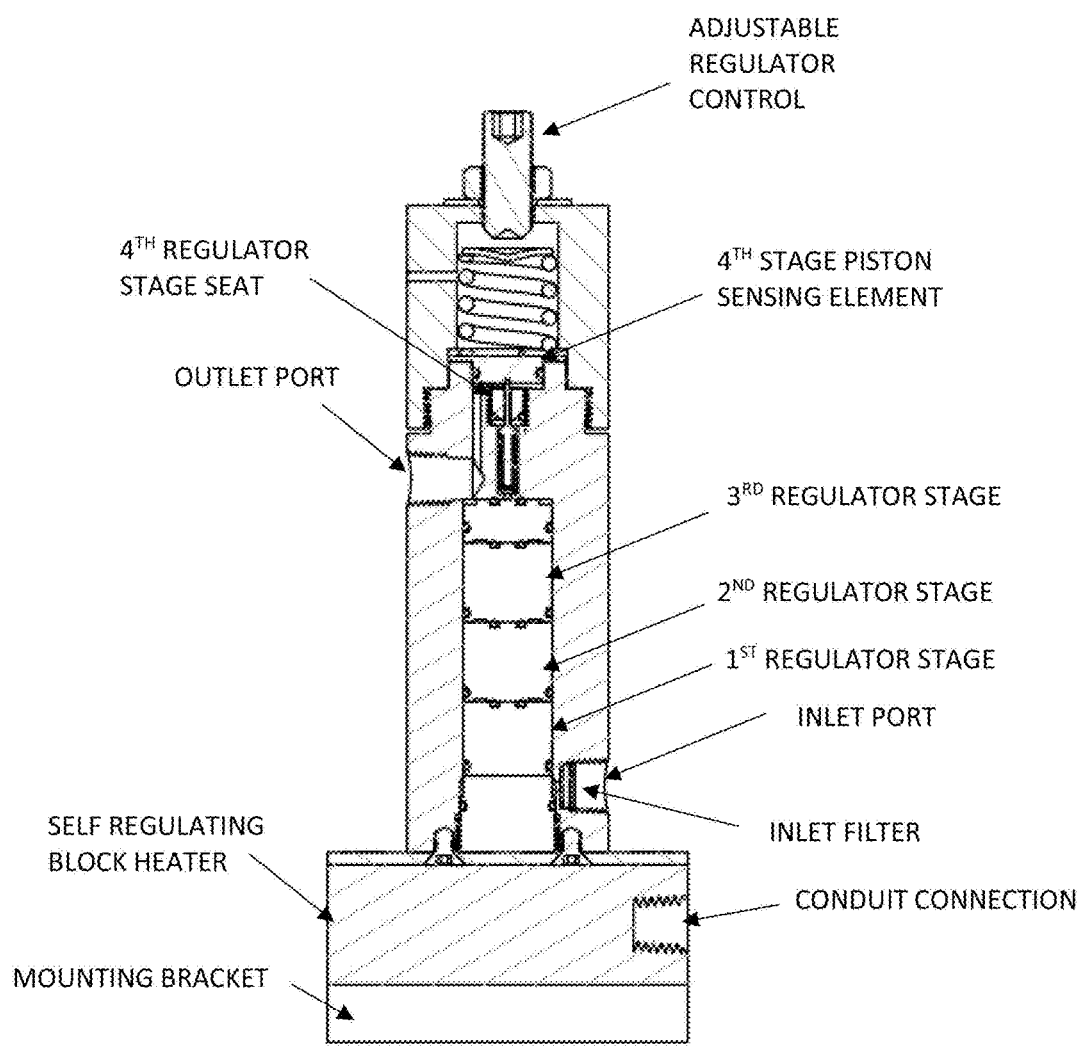
FIG. 26 is a color section view of the applicant assignee's prior art GENIE brand JTR multi-stage Heated Regulator, described in U.S. Pat. No. 8,220,479, the contents of which are incorporated herein by reference thereto.

As discussed above, applicant assignee's prior art GENIE brand Heated Regulator (FIG. 15) can be used as a component for building the present invention modular vaporizing regulator. Similarly, other components, such as the GENIE brand JTR (FIG. 26), can be mounted to the modular vaporizer modules (the vaporizer bottom 28, chamber 39, etc as disclosed herein to provide vaporizer functionality.

Figure 16:
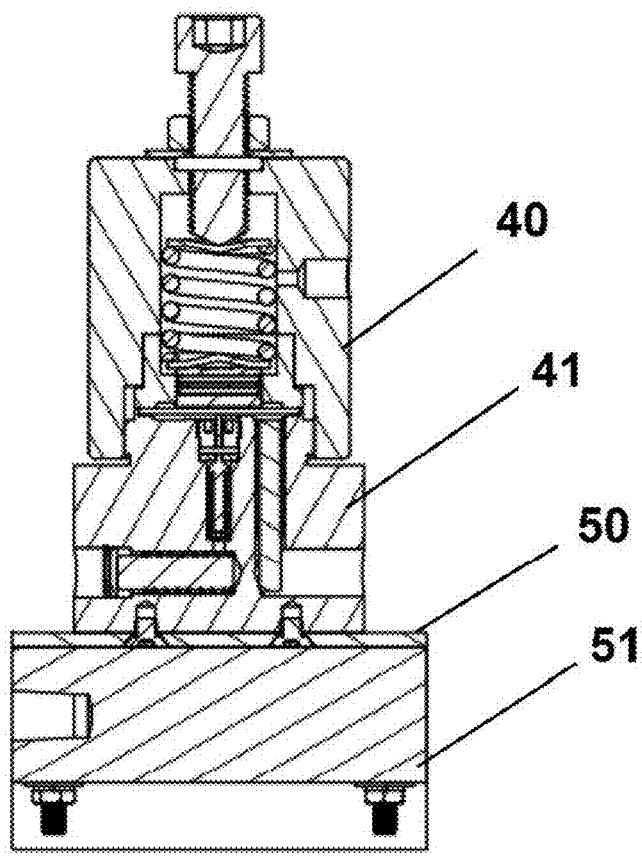
FIG. 16 is a black and white section view of the applicant assignee's prior art GENIE brand Heated Regulator (GHR) mounted to a heater block, the combination providing pre and post heat exchange.
Figure 18:
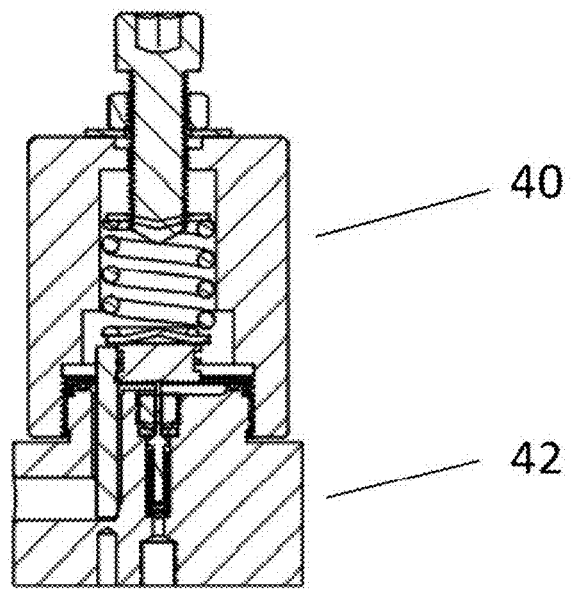
FIG. 18 is a section view of the GHR upper, with the GHR bottom section of FIG. 17 removed, and replaced with the modular vaporizer bottom (lower) of the present invention.
Figure 21:
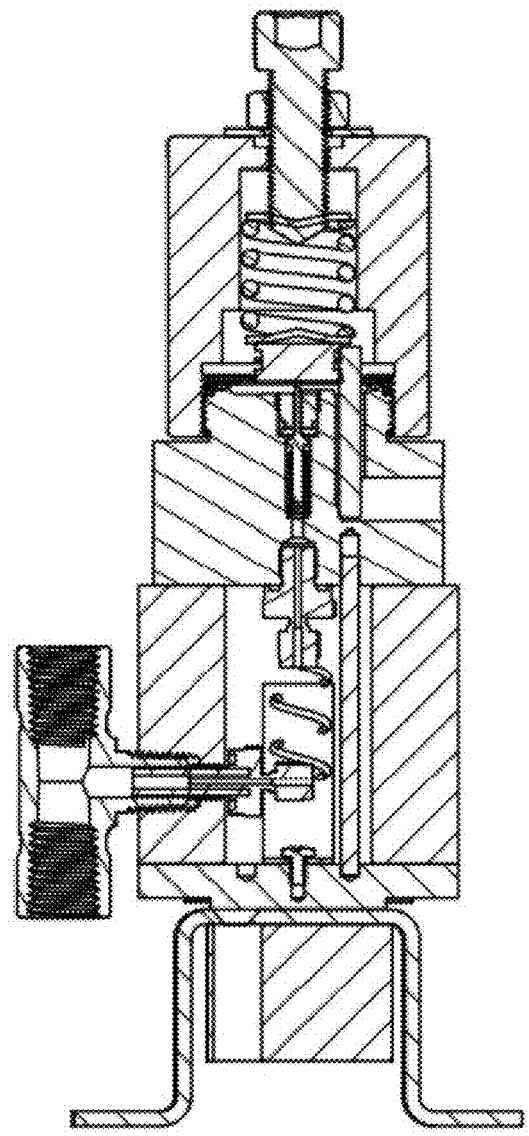
FIG. 21 is the section view of the invention of FIG. 13, without annotations.
Figure 22:
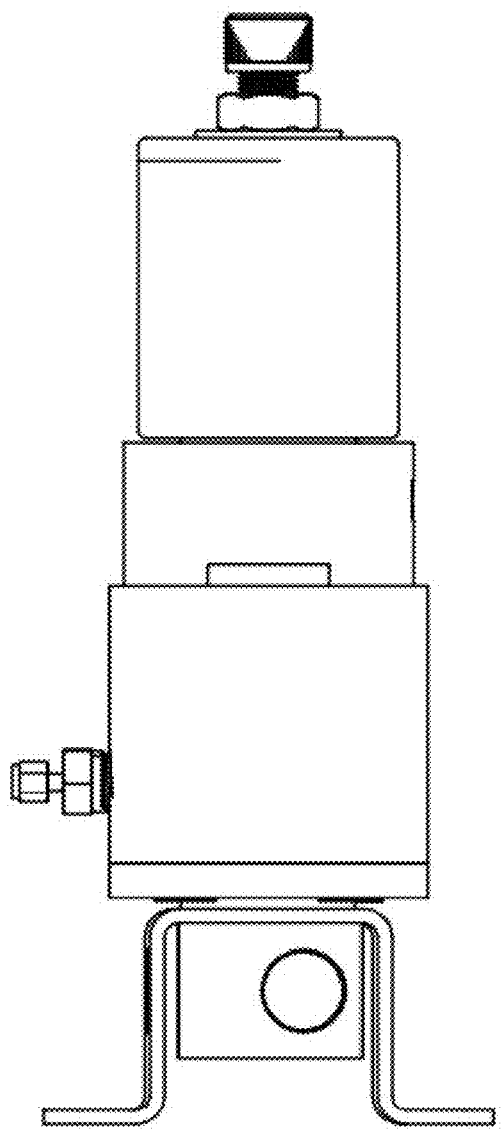
FIG. 22 is a frontal view of the first embodiment of the present invention.

For example, in the case of the Genie brand Heated Regulator, for an existing installation conversion, remove any pre-existing conduction heater block 50 and bracket 51 (FIG. 16). Next, continuing with FIG. 17, remove the heated regulator bottom 41 from the GENIE brand Heated Regulator and replace it with the modular vaporizer bottom 42 as seen in FIG. 18. Next, add the modular vaporizer chamber 39 as seen in FIG. 19. The next step is to add the modular vaporizer bottom cap 38 as seen in FIG. 20. Then, re-attach the conduction heater block 37 and bracket as seen in FIG. 21 and FIG. 28.

The modular vaporizer system described above is not intended to be limited to application with the above GHR regulator. For Example, A+ Manufacturing LLC Genie Brand JTR modular component (FIG. 26) or another modular regulator can be similarly converted to include vaporizer function. For example, in the case of the Genie Brand JTR remove any pre-existing conduction block heater and mounting bracket (See FIG. 26). Next, continuing with FIGS. 28A-28B, mount M' the JTR modular component 52 to JTR modular vaporizer bottom 48 as seen in FIG. 28A-28B. Next, add the modular vaporizer chamber 39. The next step is to add the modular vaporizer bottom cap 38. Then, attach the conduction heater block 37 and bracket as seen in FIG. 28A-B, which can be powered by power cord 34.

The components in the present invention as shown are not intended to be limiting, as other components may be utilized in the present system. For example, another embodiment of the present invention could utilize the A+ GENIE brand Membrane Separator with Liquid Block (as shown in U.S. Pat. No. 7,555,964, a CIP of 7097693 (listing the present Inventor St. Amant as second named Inventor), the contents of which are incorporated herein by reference thereto) just before the analyzer in a non-heated zone as a means of protection for use in case of power failure of the heater block resulting in liquids not being vaporized in the modular sample conditioning system.

ELEMENTS OF THE INVENTION

A—Analyzer
H—Heated area, radiant heat sink
L—Longitudinal Axis of Probe tip 3
D—Screen Disc
D'—Spring Retainer
M,'—Mounted
I—Insert
P—Power Cord Receiver
F—Flow
1—Insertion Probe
2—Gas with entrained liquids
2'—Fluid flow
3—Slotted probe tip
4—Probe isolation valve
5—Substrate coupling
6—Modular sample conditioning system
7—Regulator inlet
8—Regulator
9—Bracket—modular sample conditioning system
10—Enclosure
11—Probe passage
12—Medial area of pipe/stream
13—OD of probe
14—Rack length
15—Body
16, 16'—Insertion probe first, second ends
17, 17'—Body 15 first, second ends
18—Outer wall
19,'—slot, width
20, 20'—Outer, inner edges
21, 21'—Outflow passage
22—Threaded end
23—ID of Capillary Tube
24—Capillary Tube
25, 25'—First, second ends
26—Receiver
27—Flow component
28—Threaded aperture
28'—Screen
29—Tube bundle
30—Tube bundle cover
31—Tube bundle insulation
32—⅛" OD stainless steel sample tube
33—Heat trace with end termination
34—Power cord included in tube bundle but separate from heat trace
35—Tube bundle boot
36—Liquid Bypass
37—Conduction Heater Block, 37' Bracket, 37" Width
38—Modular Vaporizer Bottom Cap, 38' Raised center area
39—Modular Vaporizer Chamber, 39' ID
40—GENIE brand Heated Regulator Top
41—GENIE brand Heated Regulator Bottom
42—Modular Vaporizer Bottom
43—Thermal Isolation Barrier
44—Radiant Heat Sink
44, 44'—Radiant Heat Sink Extensions
45—Capillary Action Tube, 45' vaporizer outlet
46—Heat Pipe
47—Post Regulation Heat Exchanger
48—JTR Modular Vaporizer Bottom
49—Regulator Outlet Port
50—Regulator Heater Block
51—Bracket
52—JTR Modular Component configured for pressure regulation
53, 53' stacked regulator stages which can be used to provide incremental pressure reduction
54 probe outlet
55 regulator outlet
56 relief valve as modular sample conditioning component (MSC)
57 pressure gauge as MSC
58 temperature gauge as MSC
59 conduction heat heater block 37
60 radiant heat via heat sink extensions 44', 44"
61 moveable heat via heat pipe 46
62 capillary line from probe tip 54 to vaporizing regulator inlet 7
116 Probe passage ID
117,'—O-Ring
119 Capillary flow passage from probe The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A tube bundle interface for a modular conditioning system, comprising:
a heated conditioning component affixed to a mounting bracket;
a tube bundle boot affixed to said mounting bracket;
a tube bundle comprising an sample tube formed to facilitate a flow of conditioned fluid from said modular conditioning system, said sample tube being insulated, said tube bundle further comprising a power cord;
wherein said tube bundle boot is formed to receive and engage an end of said tube bundle so as to provide power to a heater for said heated conditioning component, via said power cord.

2. The device of claim 1, wherein said heater comprises a heater block associated with said heated conditioning component.

3. The device of claim 2, where said heated conditioning component comprises a vaporizer.

4. The device of claim 3, wherein said vaporizer comprises a modular vaporizing pressure regulator, having a first pressure reducing stage.

5. The device of claim 4, wherein said modular vaporizing pressure regulator has a second pressure reducing stage.

6. The device of claim 5 where said modular vaporizing pressure regulator further comprises a radiant heat sink formed to thermally engage said heater block, said radiant heat sink situated in a vaporization chamber, and a heat pipe, said heat pipe formed to transfer heat from said heater block to a component engaging said vaporization chamber.

7. The device of claim 6, wherein said modular vaporizing pressure regulator has an inlet, said modular vaporizing pressure regulator further comprising:
 a plastic tube formed to thermally isolate said inlet;
 a length of capillary tubing sized for the fluid and flow rate using the Poiseuille Equation, said capillary tubing mounted to transfer fluid from a probe to said inlet, said heater block being formed to conduct heat to said vaporizing chamber;
 a heat sink formed to provide selective transfer heat within said vaporizer;
 a internal heat pipe to transfer heat to the outlet pressure drop area of the vaporizer
 a post-heat internal heat exchanger formed to transfer heat to the outlet of the vaporizer.

8. The device of claim 7, wherein said modular vaporizing pressure regulator has a bottom cap having a raised portion forming an engagement surface to receive heat from said heater block, said raised portion corresponding to the size of said heater block and said vaporizer chamber formed so as to maximize heat transfer efficiency.

9. The device of claim 8, wherein said inlet comprises a liquid bypass port.

10. The device of claim 5, wherein said tube bundle further comprises a heat trace having a length thermally engaging said sample tube, said power cord being isolated from said heat trace and said power cord via said insulation.

11. The device of claim 10, wherein said tube bundle has a length, and a cover along said length enveloping said sample tube, said heat trace and said insulation, as well as said power cord.

12. The device of claim 5, wherein said sample tube is configured to facilitate said flow of conditioned fluid from said modular conditioning system to an analyzer.

* * * * *